United States Patent
Shehada et al.

(10) Patent No.: US 7,244,251 B2
(45) Date of Patent: Jul. 17, 2007

(54) IMPLANTED SURGICAL DRAIN WITH MULTIPLE SENSING ELEMENTS FOR MONITORING INTERNAL TISSUE CONDITION

(75) Inventors: Ramez Emile Necola Shehada, La Mirada, CA (US); Nicolas Jabbour, Pasadena, CA (US)

(73) Assignee: Alfred E. Mann Institute for Biomedical Engineering, Los Angeles, CA (US)

( * ) Notice: Subject to any disclaimer, the term of this patent is extended or adjusted under 35 U.S.C. 154(b) by 0 days.

(21) Appl. No.: 10/776,022

(22) Filed: Feb. 9, 2004

(65) Prior Publication Data

US 2004/0254432 A1 Dec. 16, 2004

Related U.S. Application Data

(60) Provisional application No. 60/453,009, filed on Mar. 6, 2003, provisional application No. 60/445,714, filed on Feb. 7, 2003.

(51) Int. Cl.
*A61M 1/00* (2006.01)
*A61B 5/0205* (2006.01)

(52) U.S. Cl. ............... 604/541; 600/549; 600/302; 607/88

(58) Field of Classification Search ........ 604/540–541; 600/300–301, 573, 302, 324, 329; 607/115, 607/149

See application file for complete search history.

(56) References Cited

U.S. PATENT DOCUMENTS

| | | | |
|---|---|---|---|
| 3,030,953 A | 4/1962 | Koehn | |
| 3,515,137 A | 6/1970 | Santomieri | |
| 3,537,451 A | 11/1970 | Beck | |
| 3,614,737 A * | 10/1971 | Sadowsky | 382/115 |
| 3,674,013 A | 7/1972 | Polanyl | |
| 3,680,562 A | 8/1972 | Wittes et al. | |
| 3,769,497 A * | 10/1973 | Frank | 377/21 |
| 3,866,599 A * | 2/1975 | Johnson | 600/342 |
| 3,989,571 A | 11/1976 | Harautuneian | |

(Continued)

FOREIGN PATENT DOCUMENTS

ES 2154241 3/2001

(Continued)

OTHER PUBLICATIONS

Buise, M.P. et al. Reflectance Spectrophotometry and Tissue Oxygenation in Experimental and Clinical Practice. Abstract only. (A printed publication published prior to Feb. 9, 2004.).

(Continued)

*Primary Examiner*—Tatyana Zalukaeva
*Assistant Examiner*—Laura C Hill
(74) *Attorney, Agent, or Firm*—Marc E. Brown; McDermott Will & Emery, LLP

(57) ABSTRACT

The present invention is directed to devices and methods of using a surgical drain, and more particularly to a surgical drain having at least one sensor for monitoring and/or recording the condition of the anatomical site or fluid emitted from the site where the surgical drain is placed. The invention may also include modifications of the surgical drain to improve stabilization or immobilization in the proximity of the anatomical site to be monitored.

21 Claims, 26 Drawing Sheets

U.S. PATENT DOCUMENTS

| | | | |
|---|---|---|---|
| 4,295,470 A | | 10/1981 | Shaw et al. |
| 4,317,452 A | * | 3/1982 | Russo et al. ............... 604/541 |
| 4,413,633 A | * | 11/1983 | Yanda ........................ 600/549 |
| 4,416,285 A | | 11/1983 | Shaw et al. |
| 4,432,365 A | * | 2/1984 | Leist .......................... 600/358 |
| 4,497,324 A | * | 2/1985 | Sullivan et al. ............. 600/549 |
| 4,523,920 A | | 6/1985 | Russo |
| 4,631,061 A | * | 12/1986 | Martin ....................... 604/318 |
| 4,654,029 A | | 3/1987 | D'Antonio |
| 4,684,694 A | | 8/1987 | Breuer et al. |
| 4,697,593 A | | 10/1987 | Evans et al. |
| 4,699,146 A | | 10/1987 | Sieverding |
| 4,703,756 A | | 11/1987 | Gough et al. |
| 4,721,115 A | | 1/1988 | Owens |
| 4,925,452 A | | 5/1990 | Melinyshyn et al. |
| 4,938,218 A | * | 7/1990 | Goodman et al. .......... 600/338 |
| 4,951,669 A | | 8/1990 | Maxwell et al. |
| 4,951,699 A | | 8/1990 | Lipman |
| 4,954,129 A | | 9/1990 | Giuliani et al. |
| 4,971,034 A | | 11/1990 | Doi et al. |
| 5,020,537 A | | 6/1991 | Gunther |
| 5,029,582 A | | 7/1991 | Leckholm |
| 5,041,108 A | | 8/1991 | Fox et al. |
| 5,097,834 A | * | 3/1992 | Skrabal ....................... 600/366 |
| 5,106,387 A | | 4/1992 | Kittrell et al. |
| 5,108,364 A | * | 4/1992 | Takezawa et al. ............. 604/43 |
| 5,202,949 A | | 4/1993 | Hileman |
| 5,215,539 A | | 6/1993 | Schoolman |
| 5,291,896 A | * | 3/1994 | Fonger et al. ............... 600/526 |
| 5,335,305 A | | 8/1994 | Kosa et al. |
| 5,335,658 A | | 8/1994 | Bedingham |
| 5,337,748 A | | 8/1994 | McAdams et al. |
| 5,349,961 A | | 9/1994 | Stoddart et al. |
| 5,360,414 A | | 11/1994 | Yarger |
| 5,392,117 A | | 2/1995 | Bellville |
| 5,421,328 A | * | 6/1995 | Bedingham ................. 600/309 |
| 5,438,985 A | | 8/1995 | Essen-Moller |
| 5,456,252 A | | 10/1995 | Vari et al. |
| 5,476,434 A | | 12/1995 | Kalb et al. |
| 5,512,045 A | | 4/1996 | Gurchumelidze |
| 5,549,579 A | | 8/1996 | Batdorf et al. |
| 5,586,553 A | | 12/1996 | Halili et al. |
| 5,645,062 A | | 7/1997 | Anderson et al. |
| 5,685,313 A | | 11/1997 | Mayevsky |
| 5,746,207 A | | 5/1998 | McLaughlin et al. |
| 5,769,791 A | * | 6/1998 | Benaron et al. ............. 600/473 |
| 5,785,658 A | | 7/1998 | Benaron et al. |
| 5,797,398 A | | 8/1998 | Bowman |
| 5,906,584 A | * | 5/1999 | Pavoni et al. ................ 600/549 |
| 5,916,171 A | * | 6/1999 | Mayevsky ................... 600/476 |
| 5,965,873 A | | 10/1999 | Simpson et al. |
| 5,987,346 A | | 11/1999 | Benaron et al. |
| 6,106,477 A | | 8/2000 | Miessel et al. |
| 6,134,460 A | | 10/2000 | Chance |
| 6,280,703 B1 | * | 8/2001 | Combs et al. ............... 424/9.1 |
| 6,334,064 B1 | | 12/2001 | Fiddian-Green |
| 6,411,838 B1 | | 6/2002 | Nordstrom et al. |
| 6,437,855 B1 | | 8/2002 | Wilson et al. |
| 6,491,682 B2 | | 12/2002 | Paderni |
| 6,547,761 B2 | | 4/2003 | Liu |
| 6,556,851 B1 | | 4/2003 | Ott et al. |
| 6,645,199 B1 | | 11/2003 | Jenkins et al. |
| 6,711,426 B2 | | 3/2004 | Benaron et al. |
| 6,751,499 B2 | * | 6/2004 | Lange et al. ................ 600/544 |
| 6,809,653 B1 | * | 10/2004 | Mann et al. ........... 340/870.28 |
| 6,882,875 B1 | * | 4/2005 | Crowley ..................... 600/407 |
| 2002/0082587 A1 | | 6/2002 | Noda |
| 2002/0120200 A1 | | 8/2002 | Brockway et al. |
| 2002/0123674 A1 | * | 9/2002 | Plicchi et al. ............... 600/300 |
| 2002/0183629 A1 | | 12/2002 | Fitz |
| 2003/0009110 A1 | | 1/2003 | Tu et al. |
| 2004/0254432 A1 | | 12/2004 | Shehada et al. |

FOREIGN PATENT DOCUMENTS

| | | |
|---|---|---|
| WO | WO92/11803 | 7/1992 |
| WO | WO 9211803 A1 * | 7/1992 |
| WO | WO03/105942 | 12/2003 |

OTHER PUBLICATIONS

Cordis (Community Research & Development Information Service). Description of Microtrans (Microprobe multi-sensor for graft viability monitoring during organ preservation and transplantation) Project. 5 pages. (A printed publication published prior to Feb. 9, 2004.).

Fertmann, J.M. et al. Measurement of Regional Perfusion and Oxygen Saturation During Human Simultaneous Pancreas-Kidney Transplantation—Correlation with Intravital Microscopy. (A printed publication published prior to Feb. 9, 2004.) Poster.

Hölzle, F. et al. Donor Site Morbidity of the Osteocutaneous Fibula Flap. Abstract only. In Abstracts of the 16th Congress of the European Association for Cranio-Maxillofacial Surgery, Sep. 3-7, 2002, Münster, Germany.

Hölzle, F. et al. Nutritive Perfusion at Donor Site After Microvascular Fibula Transfer. Abstract only. In Microsurgery. 2003; 23(4): pp. 306-312.

Hölzle, F. et al. The Radial Artery as a Carrier of the Osteocutaneous fibula Flap for Reconstruction of the Mandibula. Abstract only. In Abstracts of the 16th Congress of the European Association for Cranio-Maxillofacial Surgery, Sep. 3-7, 2002, Münster, Germany.

Kakihana, Y. et al. Effects of Ligustrazine on Hepatic Oxygenation in Isolated Perfused Rat Liver. Abstract only. In Vivo, Jan.-Feb. 1999; 13(1):pp. 29-34.

Kasler, M. et al. [Noninvasive Intraoperative Measurement of Intracapillary Hemoglobin Oxygenation and Relative Hemoglobin Concentration in Surgical Skin Flaps.] (article in German). Abstract only. In HNO, Oct. 1990; 38(10): pp. 375-378.

Krug, A. Non-Invasive Oxygen and Perfusion Monitoring. Abstract only. In Danish Microsurgical Society, Hindsgavl Congress, Mar. 21-22, 2002.

Lea Medizintechnik. Tissue Blood Supply after Transplantation of a Pedicled Flap-Microcirculation Two Days and One Week After Surgery and Flap Conditioning. Abstract only. (A printed publication published prior to Feb. 9, 2004.).

Lea Medizintechnik. Tissue Neovascularisation One Week After Transplantation. Abstract only. (A printed publication published prior to Feb. 9, 2004.).

Lea Medizintechnik. Viability of Flaps: Intra- and Postoperative Monitoring for Increase of Transplantation Success Rate. (A printed publication published prior to Feb. 9, 2004.).

Lea Medizintechnik. Postoperative Long-Term Monitoring. Abstract only. (A printed publication published prior to Feb. 9, 2004.) 3 pages.

Lea Medizintechnik. Company Profile LEA Medizintechnik GmbH. (A printed publication published prior to Feb. 9, 2004.).

Lea Medizintechnik. O2C Oxygen To See. Price List. (A printed publication published prior to Feb. 9, 2004.) 3 pages.

Lea Medizintechnik. Fields of Application of O2C Oxygen To See. (A printed publication published prior to Feb. 9, 2004.) 3 pages.

Lea Medizintechnik. What Measures O2C Oxygen To See? (A printed publication published prior to Feb. 9, 2004.) 1 page.

Lea Medizintechnik. O2C Oxygen To See: Measurements of Tissue Circulation, Saturation of Hemoglobin SO2, Local Amount of Hemoglobin. (A printed publication published prior to Feb. 9, 2004.) 6 pages.

Lea Medizintechnik. O2C (Oxygen To See): Perfusion of Tissue; Capillary-Venous Oxygen Saturation; Blood Filling of Microvessels. (A printed publication published prior to Feb. 9, 2004.) 3 pages.

Lea Medizintechnik. O2C Probes. (A printed publication published prior to Feb. 9, 2004.).

Lea Medizintechnik. Micro Probes. (A printed publication published prior to Feb. 9, 2004.).

Loeffelbein, D. et al. Combined Non-Invasive Tissue Oxygen and Flow Monitoring in Fasciocutaneous Forearm Flaps. Abstract only. (A printed publication published prior to Feb. 9, 2004.).

Mayevsky, A. et al. Real-time optical monitoring of tissue vitality in vivo. In Optical Fibers and Sensors for Medical Applications. II. I. Edt Gannot. Proceedings of SPIE, 2002; 4616:pp. 30-39.

MICROTRANS. Micro Probe Multisensor for Graft Viability Monitoring During Organ preservation and Transplantation. Company and Product Information. (A printed publication published prior to Feb. 9, 2004.) 13 pages.

Nolte, D. et al. Simultaneous Non-Invasive Fluxmetry and Tissue Oxygen Monitoring in Fasciocutaneous Flaps. Abstract only. In Abstracts of the 16th Congress of the European Association for Cranio-Maxillofacial Surgery, Sep. 3-7, 2002, Münster, Germany.

Oak Ridge National Laboratory. Science and Technology. Institution and Research Information. (A printed publication published prior to Feb. 9, 2004.).

Simonsen, M. Remote Diagnostics and Patient Monitoring Developments. (BBI at the MEDICA 2002 Exhibition). Abstract only. In BBI Newsletter, Jan. 2003.

Sommer, N. et al. Case Study: Microcirculatory Measurements in Chronic-venous insufficiency (CVI) and Lipedema With O2C (Oxygen to See)—Observation of Effectivity of Physical Therapy. (A printed publication published prior to Feb. 9, 2004.) Poster.

Stirban, Alin et al. Differential Role of Type 2 Diabetes and Cardiovascular Autonomic Neuropathy in Impaired Control of Skin Microcirculation. Poster. (A printed publication published prior to Feb. 9, 2004.).

University of Ulster. Microtrans. From News and Events Archive 2000. 2 pages.

University of Ulster. UU Unveils Lifesaving Organ Transplant Sensor Technology. May 22, 2002. 2 pages.

Vital Medical Ltd. Multiparametric Monitoring of Tissue and Body Vitality in Real time. Company and Product Information. (A printed publication published prior to Feb. 9, 2004.) 13 pages.

Wolff, K.D. et al. Hemoglobin Oxygenation of Venous-Perfused Forearm Flaps. Abstract only. In 1: Ann. Plast. Surg., Dec. 1998; 41(6): pp. 646-652; discussion pp. 652-653.

Wolff, K.D. et al. Monitoring of Flaps by Measurement of Intracapillary Haemoglobin oxygenation with EMPHO II: Experimental and Clinical Study. Abstract only. In Br. J. Oral Maxillofac. Surg., Dec. 1996; 34(6):pp. 524-529.

Wolff, K.D. et al. Cutaneous Hemoglobin Oxygenation of Different Free Flap Donor Sites. Abstract only. In Plast. Reconstr. Surg., Oct. 1998; 102(5):pp. 1537-1543.

Wolff, K.D. et al. Intracapillary Haemoglobin Oxygenation and Interstitial pO2 in Venous Flaps: An Experimental Study in Rats. Abstract only. In Microsurgery 1998; 18(5):pp. 324-330.

Maarek et al., SPIE, Advances in Laser and Light Spectroscopy to Diagnose Cancer and Other Disease, 2135:157-165, 1994.

* cited by examiner

*FIG. 5A*
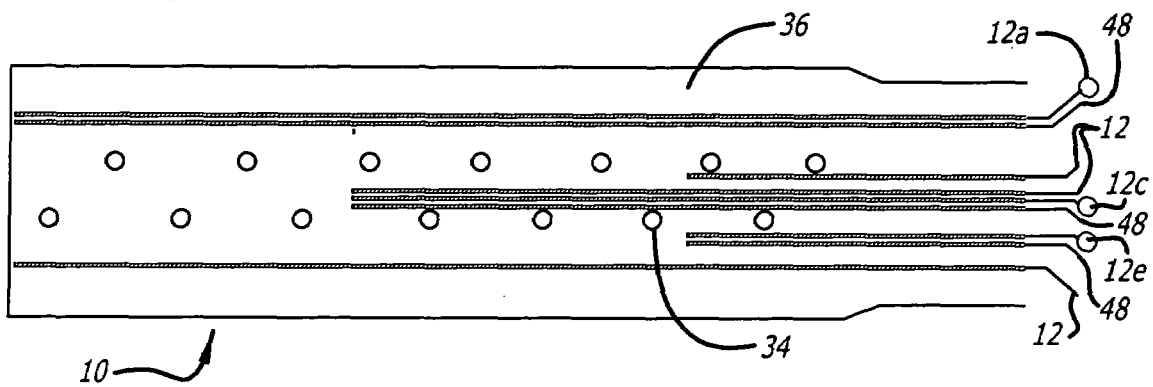
*FIG. 5B*
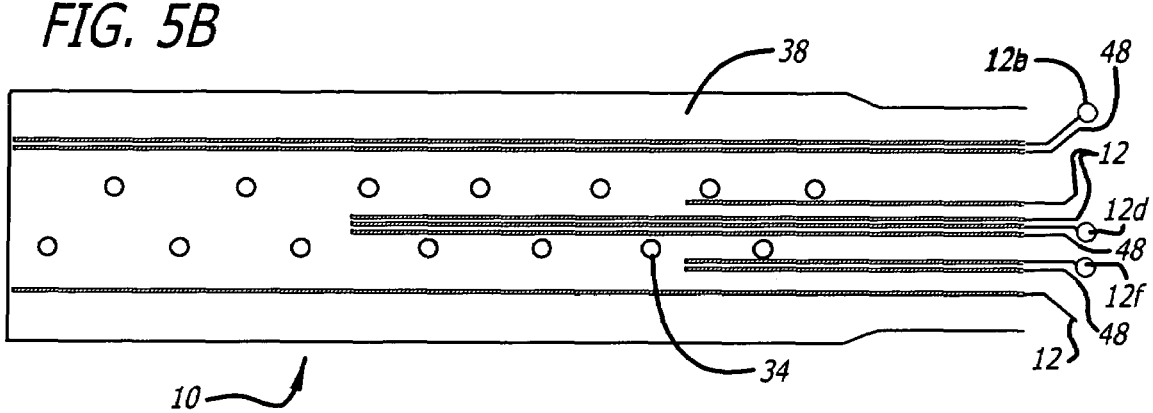
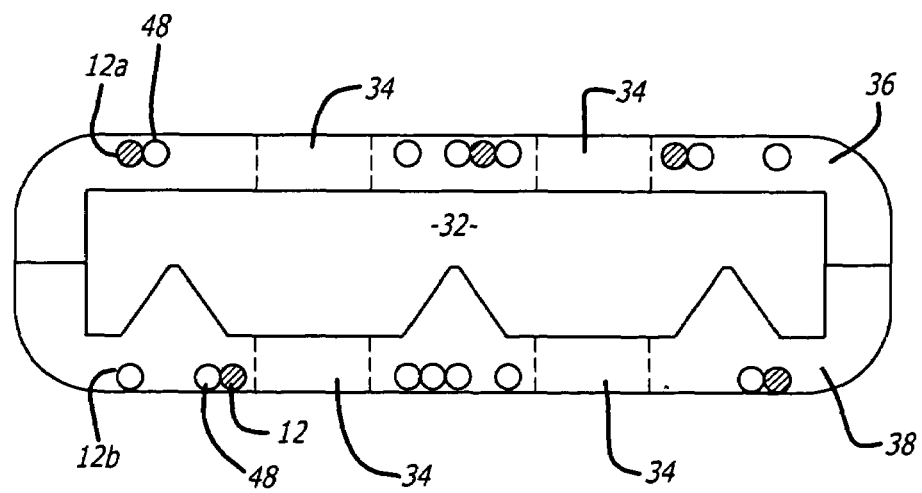
*FIG. 5C*

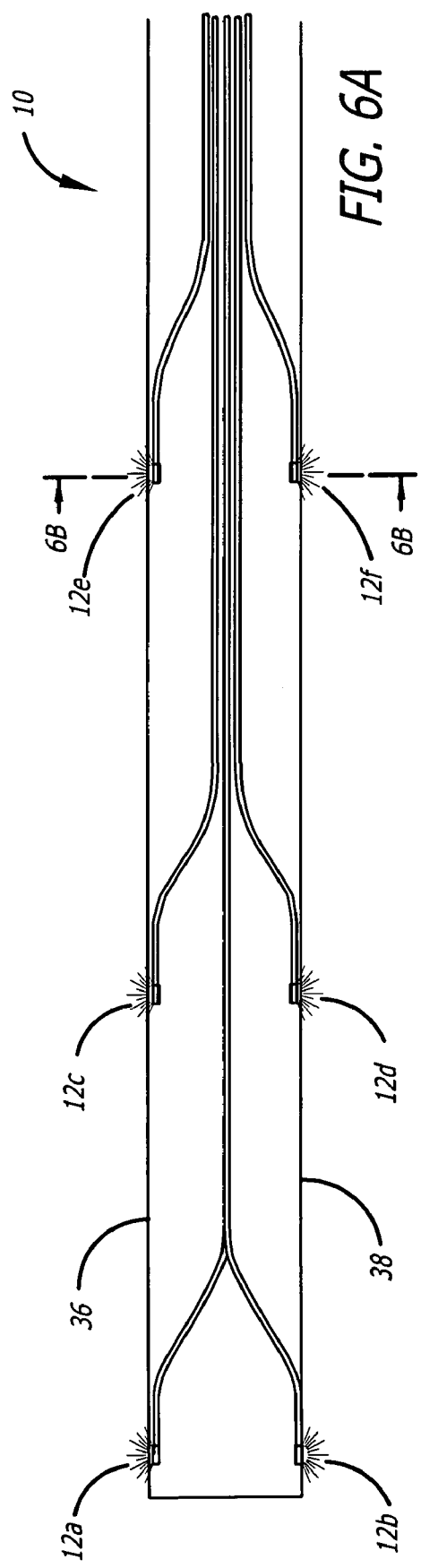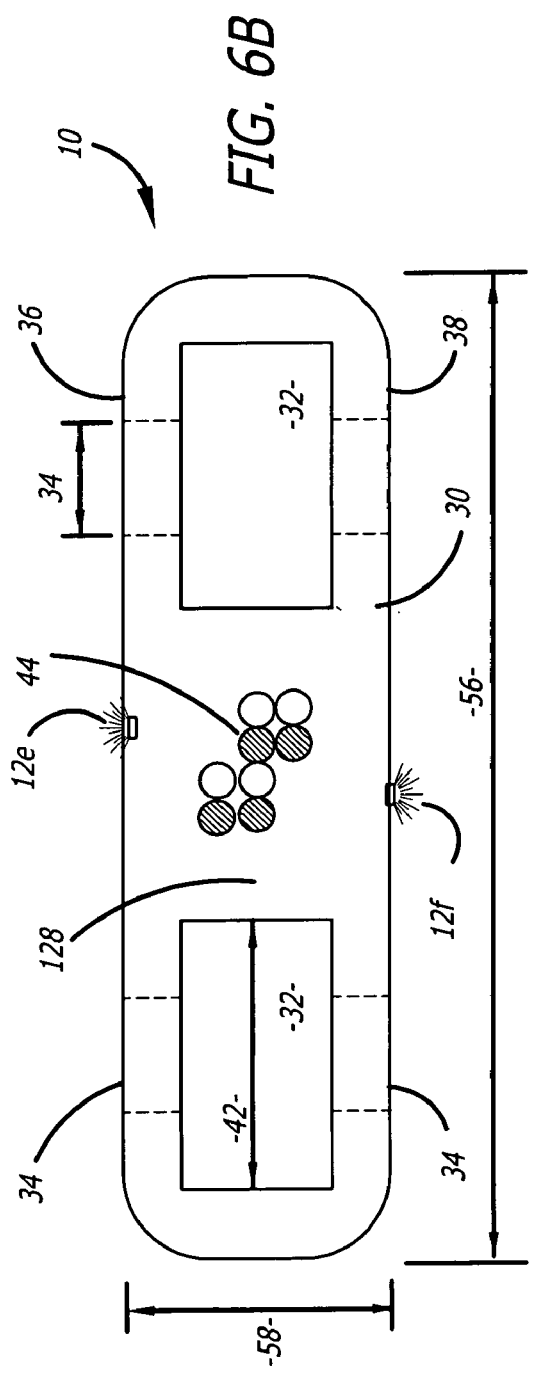

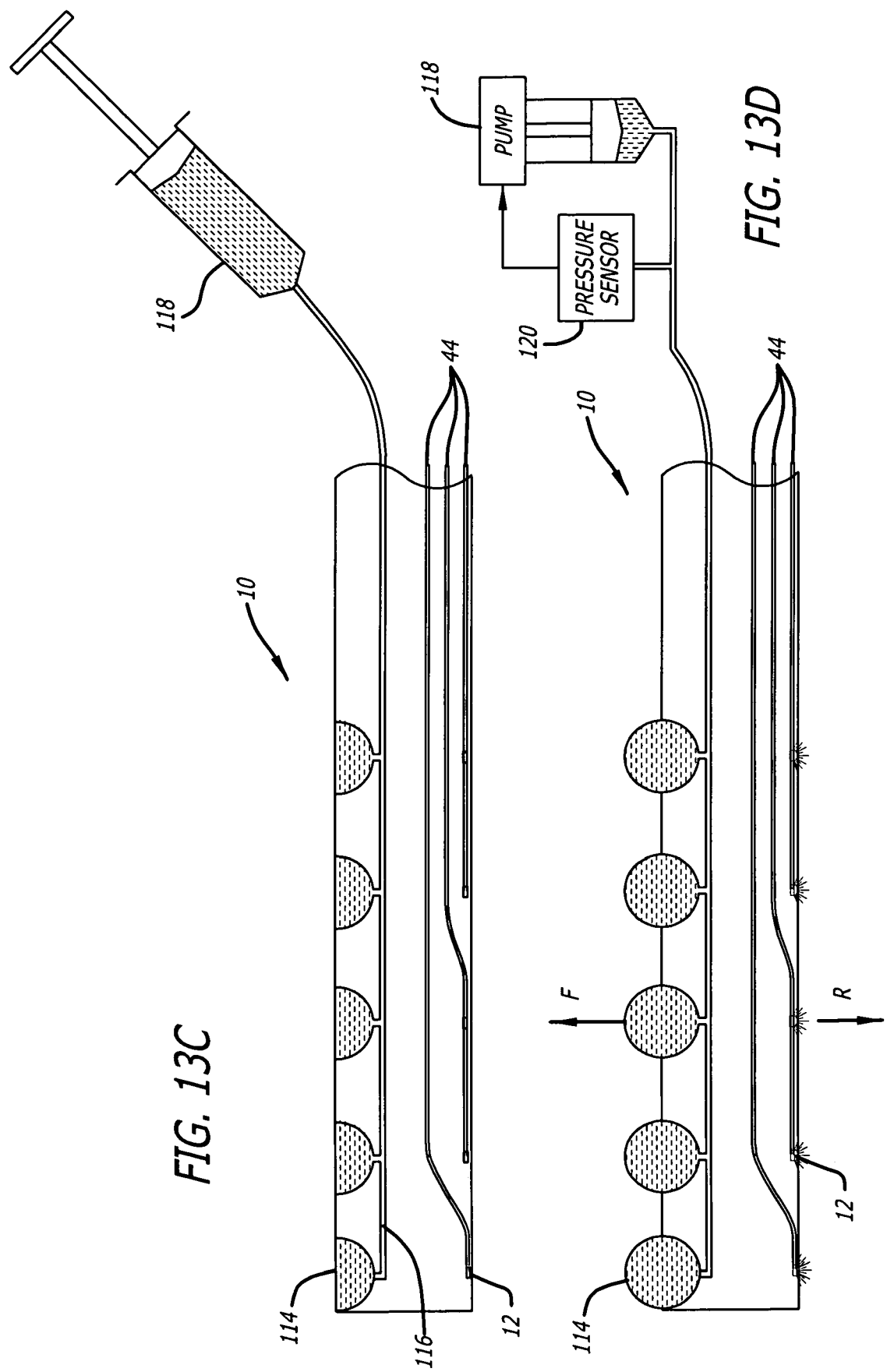

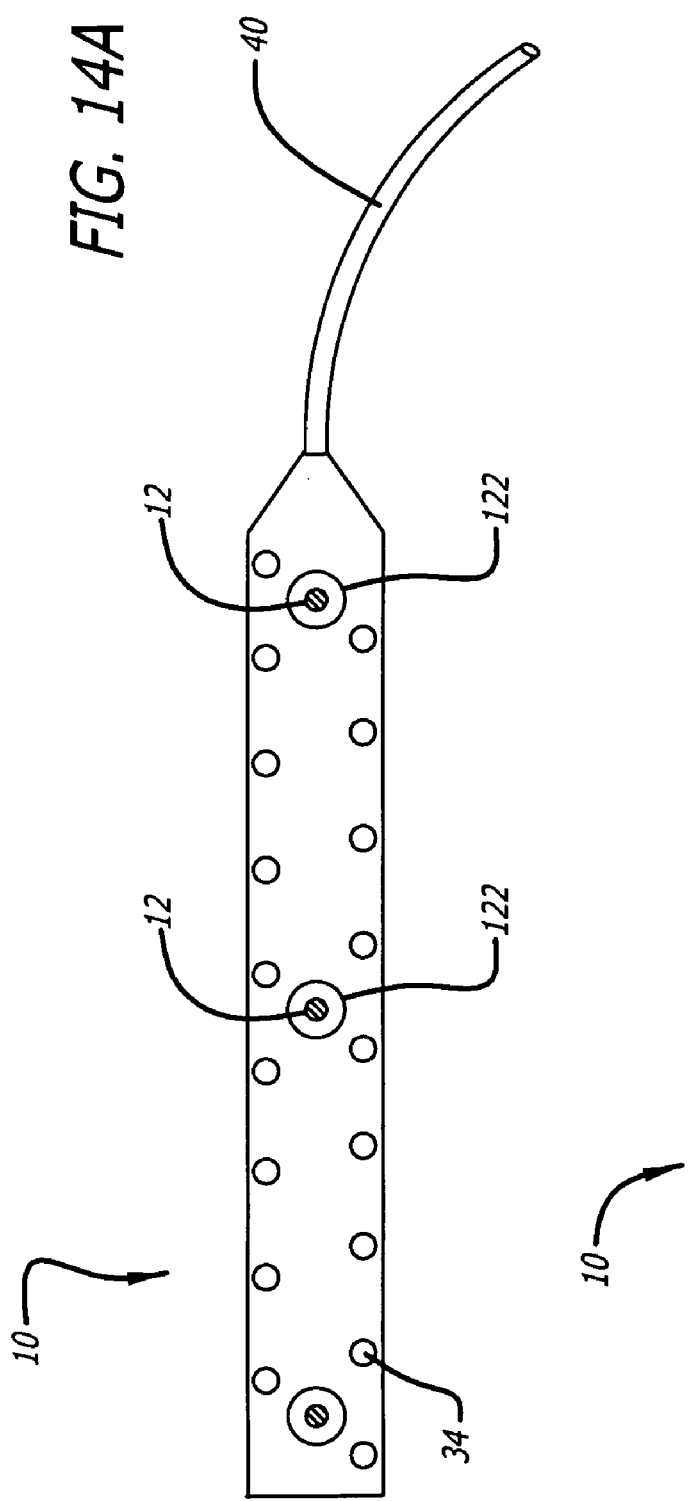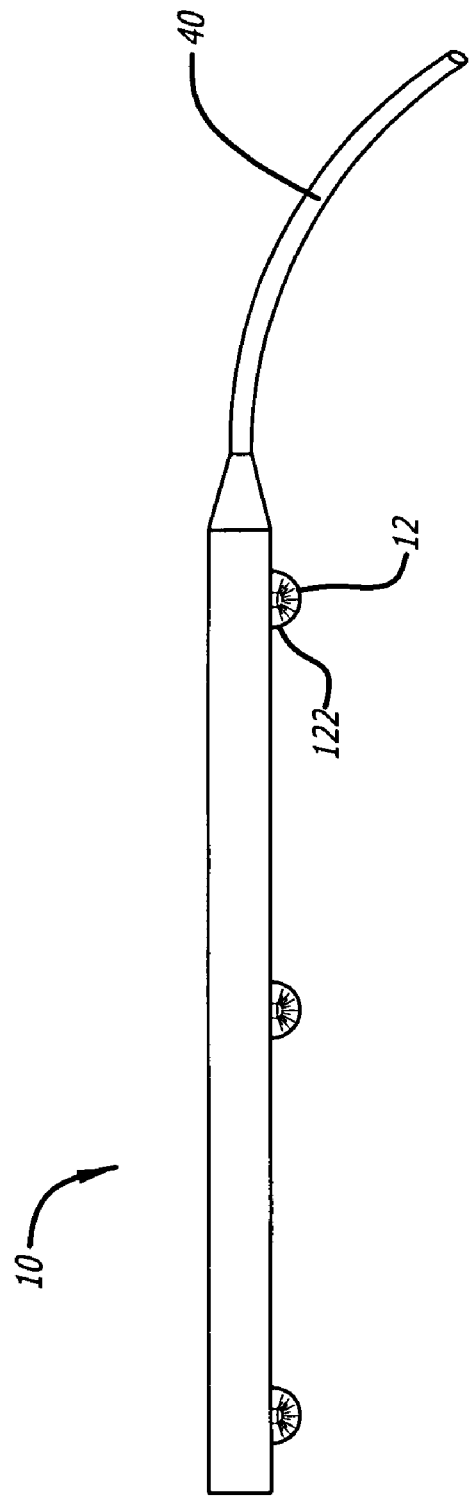

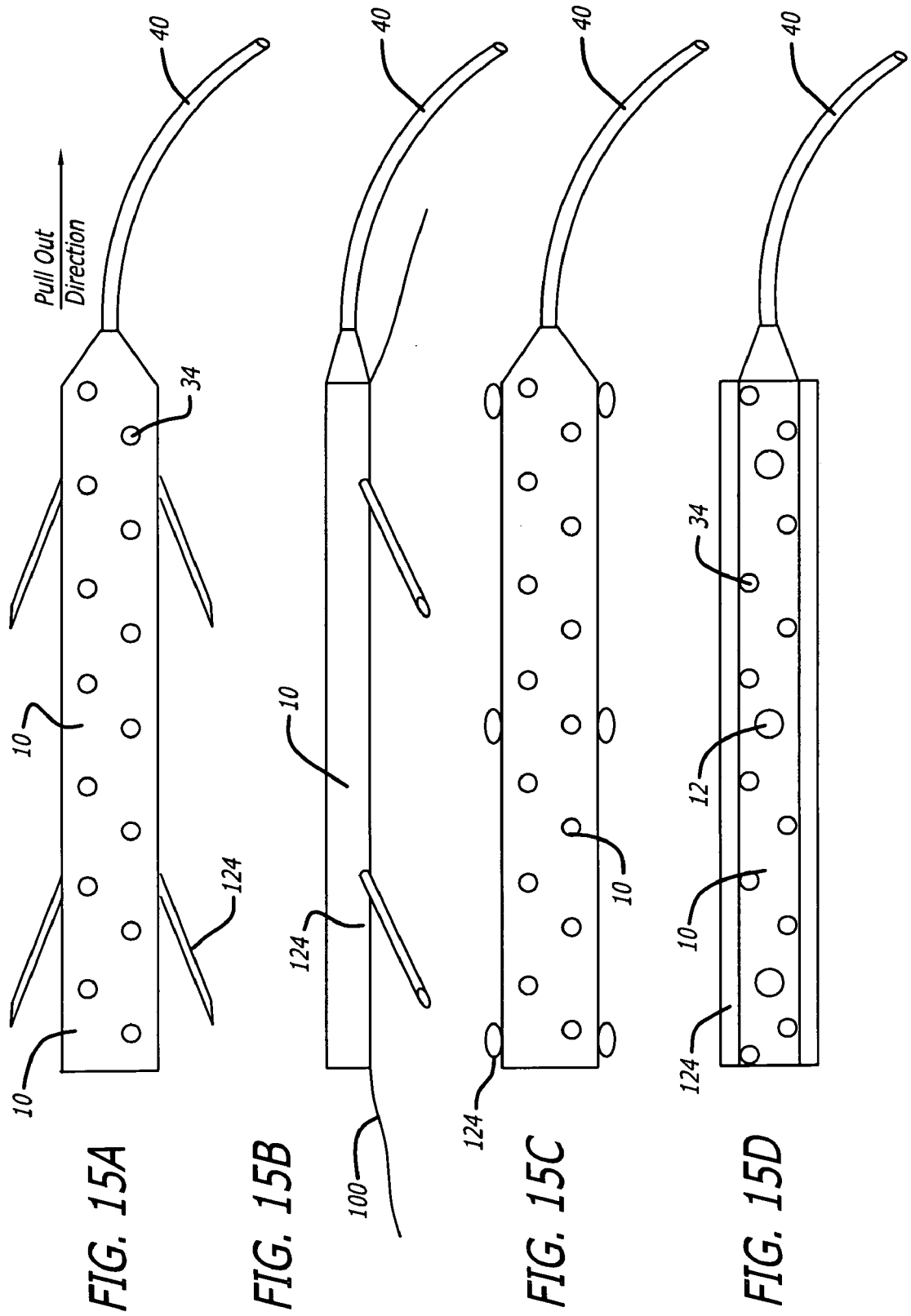

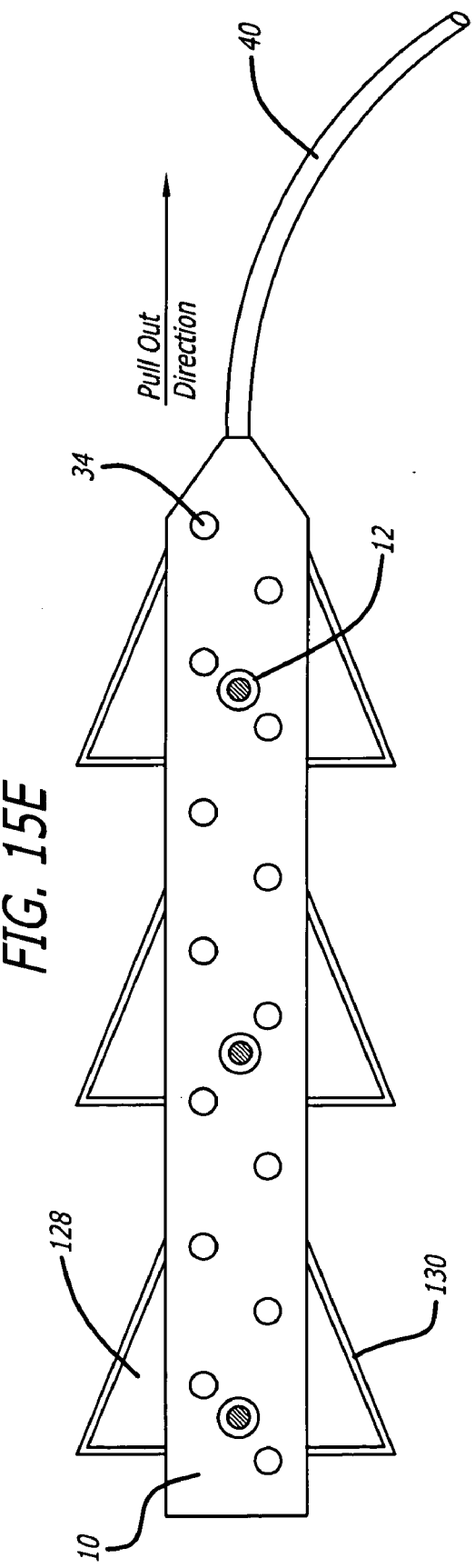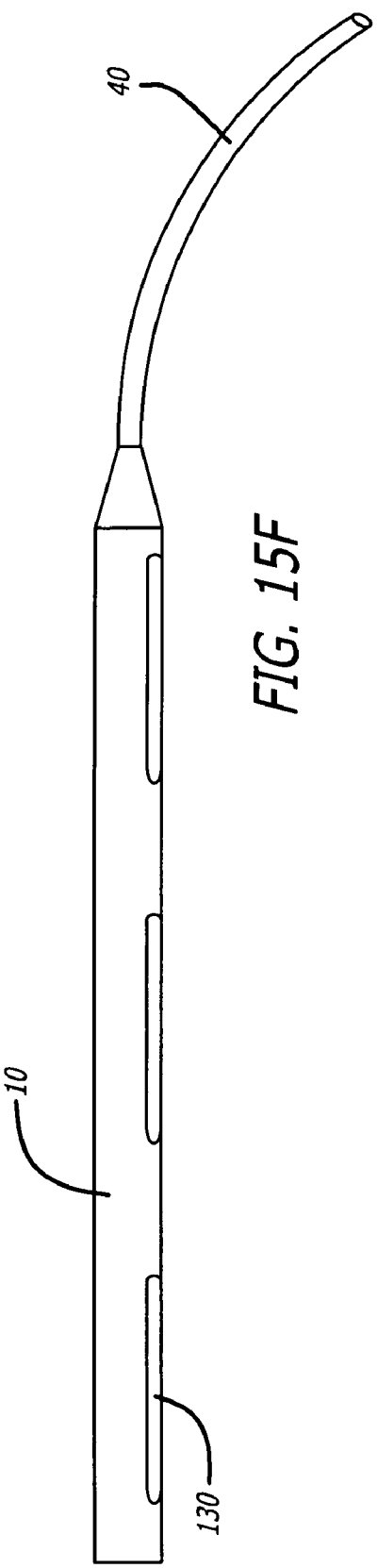

IMPLANTED SURGICAL DRAIN WITH MULTIPLE SENSING ELEMENTS FOR MONITORING INTERNAL TISSUE CONDITION

CROSS-REFERENCE TO RELATED APPLICATIONS

This application claims priority to U.S. Provisional Patent Applications 60/445,714, filed Feb. 7, 2003, and 60/453,009, filed Mar. 6, 2003, and incorporates the contents in their entirety. This application is also related to the following co-pending applications, being filed contemporaneously herewith: "Surgical Drain with Sensors for Monitoring Internal Tissue Condition," Ser. No. 11/420,702 "Surgical Drain with Sensors for Monitoring Internal Tissue Condition by Transmittance," Ser. No. 11/354,346, "Surgical Drain with Sensors for Monitoring Fluid in Lumen," Ser. No. 10/776,020 and "Surgical Drain with Positioning and Protective Features," Ser. No. 10/776,021.

BACKGROUND OF THE INVENTION

1. Field of Invention

The present invention is directed to devices and methods of using a surgical drain to monitor internal tissue condition, and more particularly to a surgical drain having at least one sensor for monitoring the condition of a tissue proximate to the surgical drain.

2. Description of Related Art

It is desirable for a physician to know the condition of tissues or organs (hereafter referred to interchangeably) within the patient's body particularly after trauma or surgical manipulation. Since such tissues may reside under the skin or within a body cavity, a physician must invasively inspect the tissue (such as by surgery, including laparoscopy), or use indirect measures to assess an organ's condition (such as radiological, blood testing and patient accounts of sensations of illness or pain). However, these methods can be disadvantageous. An invasive examination may cause discomfort and risk of infection to the patient, and the information obtained either through direct inspection or indirectly via blood or radiological analysis, may be relevant only to the time at which the procedure is performed, and examination may render only indirect information about the physiological condition of the organ.

Monitoring of organ function can be important after surgeries such as organ transplantation, resection, cryosurgery and alcohol injection. Surgical complications, such as vascular complications, may disrupt adequate oxygen circulation to the tissue, which is critical to organ function and survival. Following liver surgery, for example, a physician may draw patient blood to determine the condition of the organ by measuring liver enzymes (such as transaminases) and clotting factors (such as prothrombin). Unfortunately, these blood tests reflect liver condition only at the time the blood sample is drawn, and changes in these laboratory values can often be detected only after significant organ damage has already occurred, permitting a limited opportunity for intervention by the physician to improve the condition of the organ or find a replacement organ in case of transplantation for the patient.

Other methodologies have been used to assess internal tissue conditions. For example, (1) imaging and Doppler techniques, (2) optical techniques, and (3) thermodilution have been used to measure tissue oxygenation and/or perfusion. However, these techniques can be difficult to successfully apply to continuous monitoring of organ condition, and may provide only qualitative or indirect information regarding a condition, and/or may provide information about only a small segment of an organ.

Imaging and Doppler Methods. Angiography may be used for determining the location and extent of blood flow abnormalities in major hepatic vessels, such as hepatic artery or portal vein stenoses and thromboses. Similarly, Doppler sonography may be used for the evaluation of blood flow in the hepatic artery and the portal vein. These methods can lack the sensitivity and the resolution necessary for assessing hepatic microcirculation. Contrast sonography has been applied for qualitative assessment of blood perfusion in the microvasculature, but its potential for quantitative measurement is still unclear. Although sonography can be performed at bedside, it is neither sensitive nor specific, and does not indicate the actual tissue oxygenation. It is usually used as a screening for the more invasive angiography. Angiography is still a preferred clinical standard in determining vessel patency for any organ such as blood flow abnormalities in major hepatic vessels, such as hepatic artery or portal vein and may visualize stenosis or thrombosis in these and other vascular structure. This test however is invasive and requires the injection of contrast material with its side effect of allergic reaction, kidney failure and fluid overload. The test cannot be performed at bedside (as in Doppler Ultrasonography) and requires moving critical ill patient to the radiology suite, and the side effects are also higher in these sick patients.

Other imaging methods, such as Spiral Computer Tomography (CT), three-dimensional magnetic resonance, angiography and radionuclide scintigraphy using Technetium 99m sulfur colloid may be used to assess blood flow to organs such as the liver following liver transplantation. However, these methods may not be sufficiently sensitive to obviate angiographic assessment, as described above. Further, these methods can also be limited in their ability to measure blood perfusion in microvasculature of the tissue. Although blood may be circulating to large vessels, it is oxygenation and perfusion at the capillary level, which often maintains the health of the entirety of the organ. By the time larger vessels are visibly impaired, the organ may have already undergone significant tissue damage. Further, these methods may be invasive in requiring the infusion of dye to which patients may react. Finally, for each dye injection, the organ condition may be assessed for a given interval. If further monitoring is needed, additional dye injection and repeated imaging may be required.

Laser Doppler flowmetry (LDF) has been used to measure blood flow in the hepatic microcirculation, but may not be able to provide information about the tissue oxygenation or blood content. LDF is also limited in its application due to the short depth of penetration and the large spatiotemporal variations of the signal obtained. Therefore, this technique may not reflect information regarding a broad geography of the tissue, and large variations may occur in recordings from different areas, in spite of tissue conditions being similar between the regions.

Thermodilution. Thermodilution technology has also been used for monitoring tissue perfusion. One example is the Bowman perfusion monitor, which uses an invasive catheter probe to measure hepatic perfusion. The probe may be inserted into the liver and a thermistor in its tip may be heated to remain slightly above tissue temperature. The local perfusion may be estimated from the power used in heating the thermistor to few degrees above tissue temperature to induce local dilation of the blood vessels. This can lead to a false perfusion measurement that is higher than the actual perfusion away from the probe. The latter source of error may not be corrected by calibration because the degree of vasodilation per temperature rise may vary between patients and may depend on many factors including administered drugs.

Thermodilution techniques may also be disadvantageous at least in requiring the insertion of catheter probes into an organ, which can become impractical when multiple probes are to be used.

Perfusion detection techniques such as LDF and thermodilution have an additional common inherent limitation. These methods may not measure tissue oxygenation, which is more relevant than perfusion in determining tissue viability. Perfused tissue can still suffer ischemia, oxygen deprivation, depending on the oxygen demand by the tissue versus its availability in the blood. For example, the liver has a dual blood supply from the hepatic artery and the portal vein. The blood flowing from the portal vein into the liver carries much less oxygen to the hepatic tissue than that from the hepatic artery. An occlusion of the hepatic artery would not cause a significant drop the hepatic perfusion, however, it would cause a drastic drop in the oxygenation. Hence, monitoring the hepatic perfusion only would be a misleading measure of ischemia. Further, this critical demand-availability balance can be easily disturbed due to immunogenic and/or drug reactions, therefore monitoring of oxygenation levels is important in monitoring tissue condition.

Optical Methods. Conventional optical techniques for the detection of tissue ischemia include fluorescence and transmission methods. Ischemia leads to anaerobic respiration and the accumulation of the reduced nicotinamide coenzyme NADH. The concentration of NADH may be detected optically because it is autofluorescent and has peak excitation and emission wavelengths at about 340 nm and 470 nm, respectively. Therefore, the fluorometric properties of NADH can be used to monitor and quantify this marker of ischemia.

However, this technique may not have been applied clinically due to several concerns. First, the fluorescence of NADH can be strongly modulated by the optical absorption of tissue hemoglobin, and the absorption of hemoglobin varies with its state of oxygenation, which can complicate the analysis of the data. These modulations can mask the actual intensity of NADH fluorescence thereby causing inaccuracies in the evaluation of ischemia. Further, this method may be disadvantageous at least in that repeated exposure of the tissue to ultraviolet light results in photobleaching of the tissue. Therefore, it may not be possible to continuously monitor the same position on the organ for a prolonged period of time (i.e., more than 24 hours). Finally, the above method is only an indirect evaluation of,tissue ischemia, as it relies on monitoring abnormalities in the concentration of NADH and may result from other conditions such as generalized sepsis or hypotension.

Optical transmission methods involve the use of visible and/or near-infrared radiation to measure the absorbance of blood in a tissue bed and determine the oxygen saturation of hemoglobin. A common transmission technique is pulse oximetry where red and infrared light from light emitting diodes is transmitted through the tissue, usually a finger or ear lobe, and detected by a photodiode. The oxygen saturation of hemoglobin can be estimated by measuring its optical absorption at predetermined wavelengths that allow the maximum distinction between oxyhemoglobin and deoxyhemoglobin. Researchers have used lasers to illuminate one side of the kidney and detected the transmitted light on the opposite side using a photomultiplier. For example, Maarek et al., SPIE, *Advances in Laser and Light Spectroscopy to Diagnose Cancer and Other Disease*, 2135:157-165, 1994. A major disadvantage of such techniques is the invasive nature of the procedure to place a tissue sample between the light source and the detector for a single measurement.

Intra-abdominal pressure following major surgery or trauma (such as a car accident, gun shot wounds, combat, or earthquake injuries) may rise to extremely high levels due to tissue edema secondary to the injury, especially following multiple blood transfusions, severe shock or inflammatory responses.

An increase in pressure may lead to severe organ dysfunction, such as kidney failure and acute respiratory failure due to lung compression through the diaphragm. The increased pressure in the abdomen may also lead to a decrease in the venous returns to the heart, therefore, affecting the cardiac output and the perfusion to all organs/tissues leading to a decrease in oxygen delivery.

Early detection of critical intra-abdominal pressure may be corrected by several interventions, including sedating the patient or opening of the abdomen. Prompt restoration of proper intra-abdominal pressure can reverse the consequences described above. However, once a critical point is reached, organs may suddenly fail, which may be irreversible in certain conditions and lead to rapid deterioration of multiple organs and potentially death.

A current method of monitoring intra-abdominal pressure following major surgery or trauma relies on indirect measurement of intra-organ pressure such as the bladder or the stomach pressure. These methods require direct operator intervention and are done only intermittently at a specific timing, such as every 1 to 4 hours, or if the patient shows signs of deterioration.

Current methods of measuring abdominal pressure may carry significant errors due to direct personal intervention, lack of reproducibility and challenges related to the injury itself. For example, a large hematoma or pelvic fracture may affect the bladder pressure directly without relation to the overall intra-abdominal pressure.

As discussed above each of these methods has significant technical disadvantages to monitoring tissue condition. Further, each of these methods can also be cumbersome and expensive for bedside operation due to the size of the apparatus and cost associated with staff administering these methods, and unsuitable for continuous monitoring of tissue conditions.

Therefore, it is desirable to have a device and methods to aid physicians in predicting problems and complications associated with internal trauma or surgery. It is desirable to have a device which is positionable and removable with relatively minimal effort, minimally invasive and causes minimal discomfort for the patient, provides continuous current information about tissue or organ condition, provides direct information about tissue or organ condition, and/or provides feedback on the effects of interventions, such as medications or other procedures to improve tissue or organ condition.

BRIEF SUMMARY OF INVENTION

In one embodiment of the invention, a surgical drain may be used for postoperative monitoring of the condition of a tissue and/or organ, generally or a transplanted organ, more specifically.

In one embodiment of the invention, a surgical drain may be used to provide continuous intraoperative and/or postoperative information on the physiological condition of a tissue including perfusion and/or oxygenation.

In one embodiment, a surgical drain may be configured for ease of application by a physician, as well as ease of removal when monitoring is no longer required.

These, as well as other objects, features and benefits will now become clear from a review of the following detailed description of illustrative embodiments and the accompanying drawings.

BRIEF DESCRIPTION OF DRAWINGS

FIGS. 3A-F are bottom views of embodiments of a surgical drain; FIGS. 3D & E are end views of embodiments of a surgical drain.

FIGS. 5A & B are schematic diagrams of a top and bottom plan view of one embodiment of a surgical drain, respectively; FIG. 5C is a schematic diagram depicting a cross-sectional view of one embodiment of a surgical drain.

FIG. 6A is a schematic diagram of a side view of one embodiment of a surgical drain; FIG. 6B is a schematic diagram depicting a cross-sectional view at A-A of the embodiment shown in 6A.

FIG. 14A is a schematic depiction of a bottom view and FIG. 14B is a schematic depiction of a side view of one embodiment of a surgical drain having protrusions thereon.

FIGS. 15A-F are schematic diagrams of embodiments of surgical drains modified to improve stability of the drain relative to the tissue monitored.

DETAILED DESCRIPTION OF ILLUSTRATIVE EMBODIMENTS

Figure 1A:
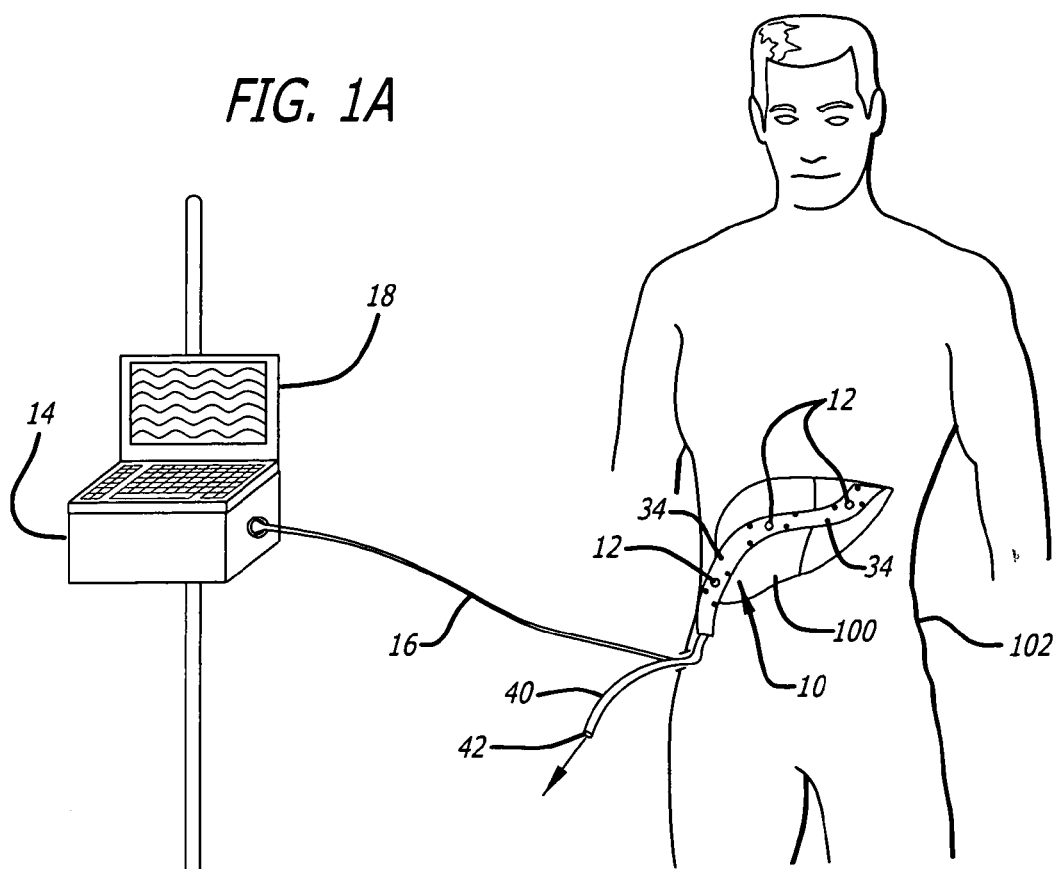
FIG. 1A is a schematic diagram of one embodiment of a surgical drain in use having at least one sensor.

FIG. 1A is a schematic diagram depicting one embodiment of a surgical drain in use having at least one sensor. As shown in FIG. 1A, the device may include a surgical drain 10 configured for implantation within the patient's body proximate to a tissue and/or organ 100 of interest having at least one sensor or receiver 12.

The surgical drain 10 may include one or a plurality of sensors 12 in communication with a monitor 14, such as via a data cable 16. The monitor 14 may also include a display 18 configured to depict information obtained from the sensor 12. The surgical drain 10 may be in communication with a tube 40 having a conduit lumen 42, such that the fluids passing from the body in the drain lumen 32 may be transported out of the body 102 via the conduit lumen 42. The tube 40 may be formed integrally or as separate piece attached to the surgical drain 10.

Figure 1B:
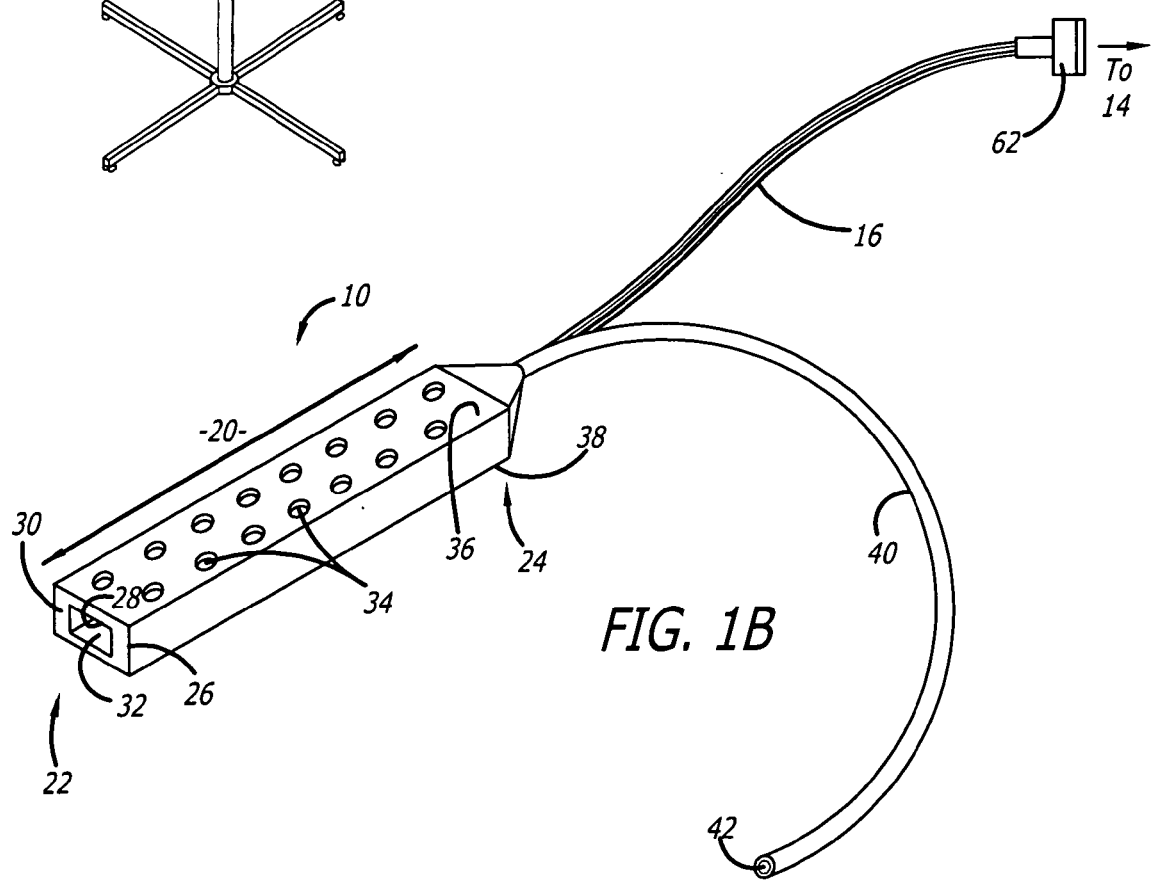
FIG. 1B is a schematic diagram depicting one embodiment of a surgical drain.

FIG. 1B is a schematic diagram depicting one embodiment of a surgical drain 10. As shown in FIG. 1B, the surgical drain 10 may have a drain length 20, extending from the drain distal end 22 to the drain proximal end 24. The surgical drain 10 may have an outer surface 26 and a drain inner surface 28 and a drain wall 30 extending from the drain outer surface 26 to the drain inner surface 28. The drain wall 30 may be in any cross-sectional shape, such as rectangular, round, oval. The surgical drain 10 may include a drain lumen 32 extending the drain length 20, and the drain lumen 32 may be open or closed at the drain distal end 22. The surgical drain 10 may include at least one or a plurality of drain holes 34 extending through at least one location on the drain wall 30. The surgical drain 10 may include approximately a drain upper surface 36, and a drain lower surface 38, and may include drain holes 34 on the drain upper surface 36 and/or lower surface 38.

A surgical drain 10 may be in the form of an elongated conduit and a flexible drain wall 30, having a substantially flat cross section having at least one internal rib 128 as shown in FIG. 5C) within the drain lumen 32, and a pattern of drain holes 34 along at least a portion of the drain length 20, such as along at least half of the drain length or along the entire drain length 20. The conduit may be in the form of a linear conduit or any shape, including but not limited to circular, square or triangular form.

An internal rib 128 may act to prevent the drain wall 30 from collapsing into the drain lumen 32 even when the surgical drain 10 is subject to a very high vacuum and/or strong lateral compression forces due to body movements of the patient and the healing process at the drainage site. An internal rib 128 may also wipe back and forth across the opposite drain wall 30 to keep the conduit lumen 32 and drain holes 34 clear when the drain walls 30 are moved laterally relative to one another. An internal rib may extend partially into the drain lumen (as in FIG. 5C) or across the entire lumen (as in FIG. 6B), for example.

The surgical drain 10 may be made of any material suitable for implantation within the body 102. The material may be selected so as to be minimally allergenic, for example. A surgical drain 10 which may be used in this invention may include a standard surgical drain. By way of example, the surgical drain 10 may be of a biocompatible silicone, latex rubber, polyvinyl chloride (PVC) or teflon of any color, and may be entirely or partially transparent. This may be advantageous in that transmitting and receiving elements may be positioned within the drain wall. In one embodiment, the optical fibers 44 may transmit light to a fiber distal aperture proximal to the surgical drain 10 and irradiate a tissue 100, and a second optical fiber distal aperture may collect the returned light via an optically transparent window in the drain wall 30.

Figure 1C:
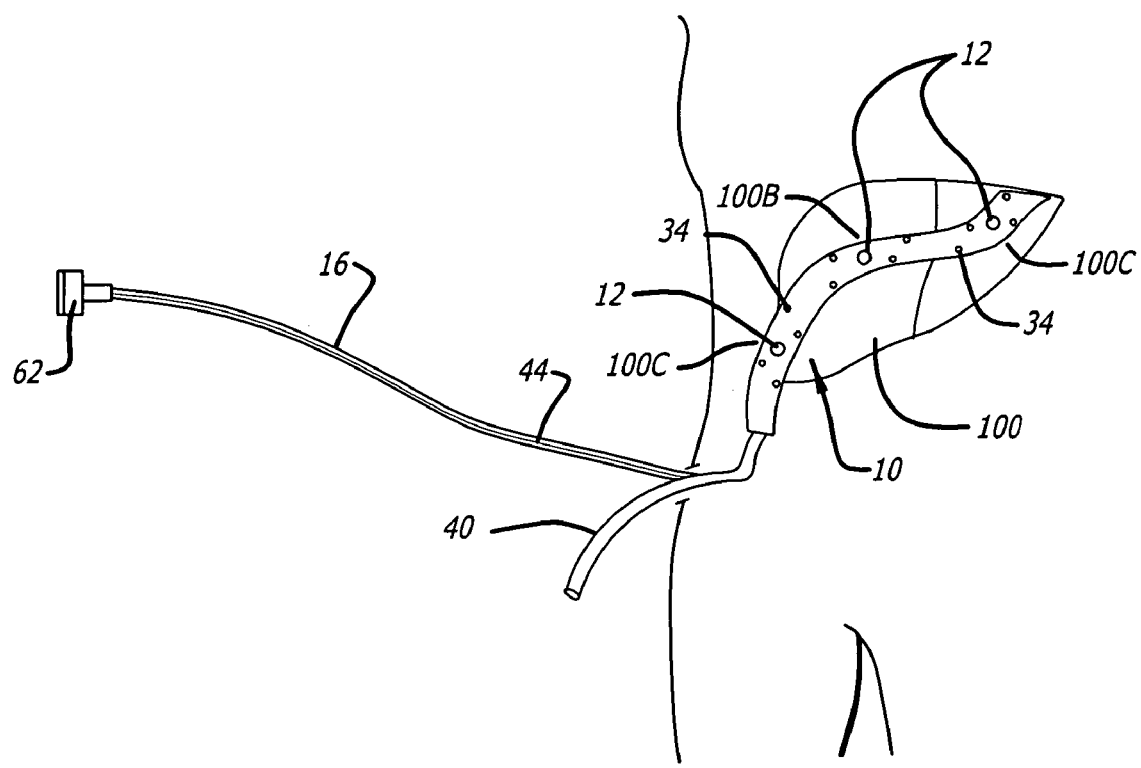
FIG. 1C is a scheatic diagram of one embodiment of the surgical drain in use having a plurality of sensors.

FIG. 1C is a schematic diagram depicting one embodiment of a surgical drain 10 in use having a plurality of sensors 12. The surgical drain 10 may include electrical transmitters and/or sensors, and/or fiberoptic transmitters and/or sensors. A corresponding wire or fiber from each sensor 12 may run along the drain length 20 and exit the surgical drain 10 as a data cable and/or multi-fiber bundle 16 that couples the sensor 12 to a monitoring system 14. Examples of connectors 62 which may be used to couple the sensor to the monitoring system are described with reference to FIGS. 8A & B below.

Figure 2A:
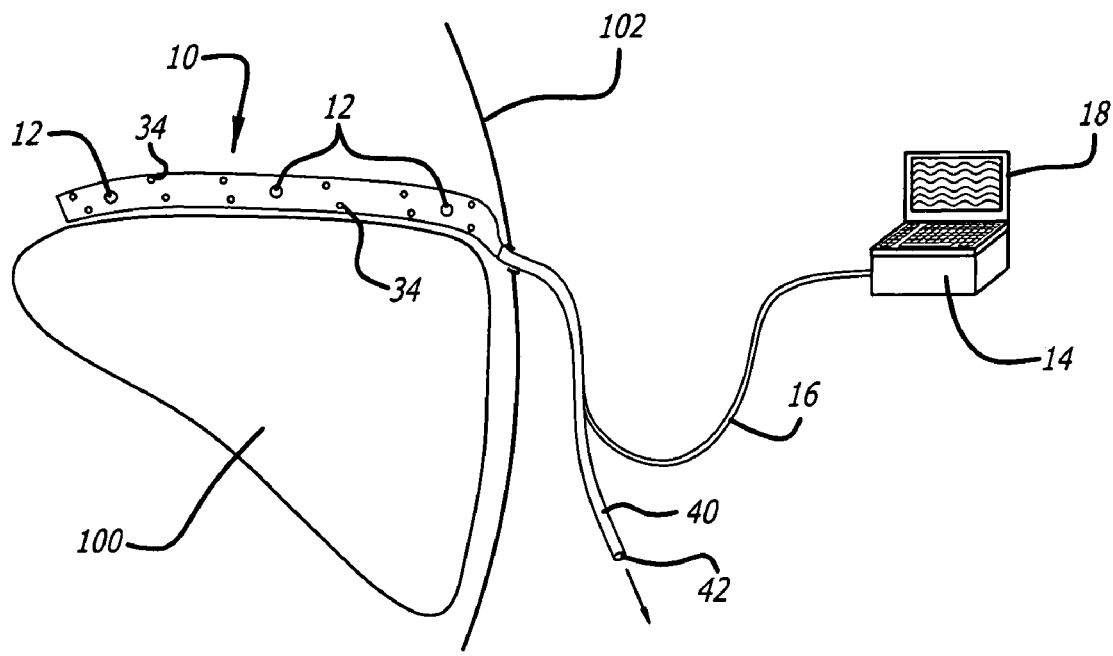
FIGS. 2A & B are each schematic diagrams each of one embodiment of the invention.
Figure 2B:
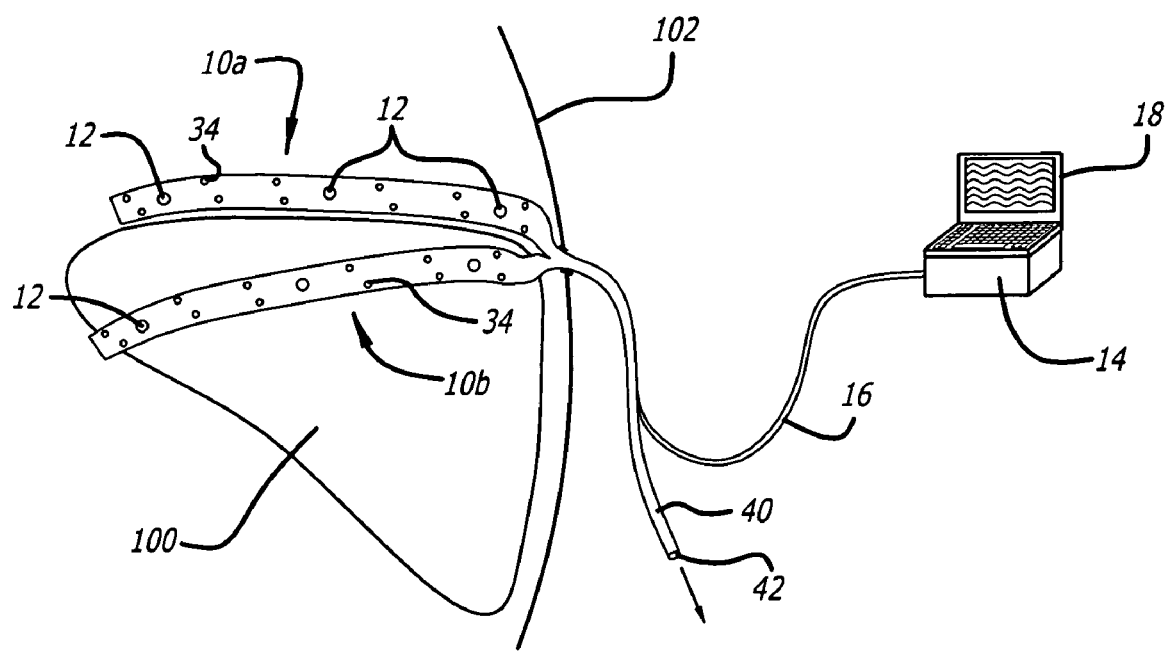

FIGS. 2A & B are schematic diagrams of each of one embodiment of the invention. The surgical drain 10 may include at least one or a plurality of sensors 12. As shown in FIG. 2A, the surgical drain 10 may include a plurality of sensors 12 spaced along the drain length 20 to permit the monitoring of different locations of a tissue 100 A, B & C to be monitored. As shown in FIG. 2B, the surgical drain 10 may have a plurality of drain branches 10a/b to accommodate monitoring larger wounds, tissue beds or tissues 100. Finally, in one embodiment, a plurality of separate surgical drains 10 may be used to monitor a single organ or a plurality of organs 100 at the same time.

The surgical drain may include a sensing system configured to sense a physiological property of a tissue 100 proximate to a surgical drain 10. In some embodiments, the sensing system may include sensors 12 which are positioned proximate to the surgical drain 10 and tissue. In some embodiments, transmitting elements 48 and receiving elements 12 may be configured to deliver energy and receive energy, for transmission to another portion of the sensing system to sense a physiological property of a tissue. The energy may include, but is not limited to, light, heat and ultrasound. It is to be understood that sensor 12 may refer to either a sensor, such as an electrical sensor, or a receiving element such as a fiberoptic proximate to the surgical drain 10. The sensors 12 may be positioned proximate to a tissue 100 for which monitoring is desired, and the sensors 12 may be configured to receive and/or detect parameters regarding the condition of the tissue 100, fluid proximate to the tissue or flowing into the surgical drain 10 therefrom. The surgical drain 10 may include at least one sensor 12 in contact with the surgical drain 10. For example, the sensor 12 may be on the drain outer wall surface 26, drain inner wall surface 28 or within the drain wall 30. The drain wall 30 may be modified to include a groove 46 to accommodate the sensors 12, transmitter 48 and/or wires/fibers 44 extending therefrom.

The sensor 12 may be situated such that at least a portion of the sensor 12 is in contact with the monitored tissue 100 or in proximity to the tissue 100, or in contact with interstitial fluids therefrom so as to probe the condition of the adjacent tissue.

A sensor 12 may be configured to detect physiological parameters, which permit the measurement of tissue oxygenation, perfusion, haemoglobin content, color, temperature, pressure, pH, respiratory coenzymes (such as NADH), local exogenous drug levels, mechanical properties (such as turgidity) and biochemical composition of the fluid within the surgical drain (such as hemoglobin, puss, bile, intestinal contents, etc.).

By way of example, pH sensors 12 may be used to detect changes in ion concentration in fluids surrounding a tissue 100 or within a drain lumen 32. For examples of pH sensors that may be useful in this invention, see U.S. Pat. No. 5,916,171 to Mayviski, herein incorporated by reference.

In one embodiment, a temperature sensing system may be used to detect the temperature of a tissue 100. For example, a fiberoptic thermometer may be used. The fiberoptic may transmit an excitation light pulse to the fiber distal end in proximity to a tissue 100, causing it to fluoresce. The fiber distal end may include a nonconductive phosphor tip. The fluorescent signal may be transmitted back to a photodetector by the same fiber. The fluorescent decay time may be measured by a multipoint digital integration decay curve, used to correlate the decay curve with a temperature value.

In one embodiment, a pressure sensing system may be used to detect the pressure within a body cavity, such as the abdominal cavity. For example, a fiberoptic pressure sensor may be used, and may include a pressure sensing element such as an optical interferometer at a distal tip of a fiber, and interferometric integration may be used to sense and monitor pressure over time. For examples of integration methods, see U.S. Pat. Nos. 5,392,117 and 5,202,949, herein incorporated by reference.

Figure 3A:
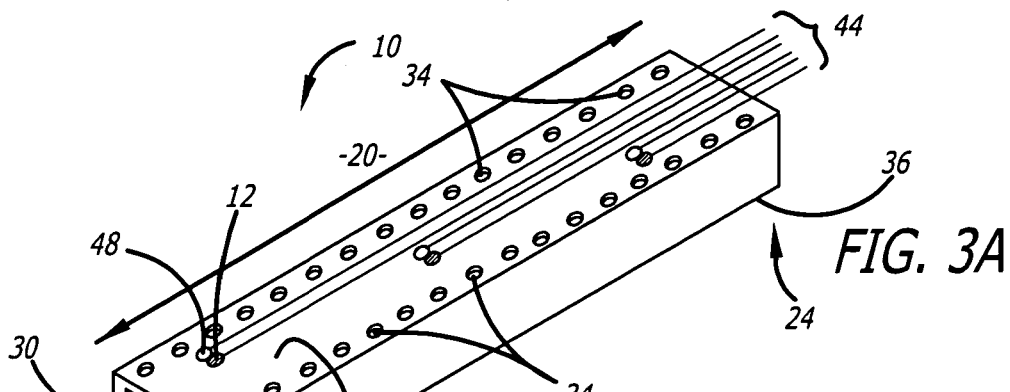
FIGS. 3A-F are schematic diagrams depicting views of embodiments of the surgical drain according to the invention.

FIGS. 3A-F are schematic diagrams depicting views of embodiments of the surgical drain according to the invention. FIG. 3A depicts a bottom view of one embodiment of a surgical drain 10 including at least one sensor 12 proximate to the drain lower surface 38. The surgical drain 10 may further include at least one transmitter 48 for delivering energy, such as light, including white light, to the monitored tissue 100, in the proximity of the at least one sensor 12. The surgical drain 10 may further include a plurality of pairs of transmitters 48 and sensors 12 located along the surgical drain length 20 so as to detect information from different regions of the organ 100, as shown in FIG. 1C, for example.

By way of example, as shown in FIG. 3A, a sensor 12 in proximity to a transmitter 48 may be used to collect derived energy, including the reflectance or diffuse reflectance from, or transmitted energy through the tissue 100 monitored.

Figure 3B:
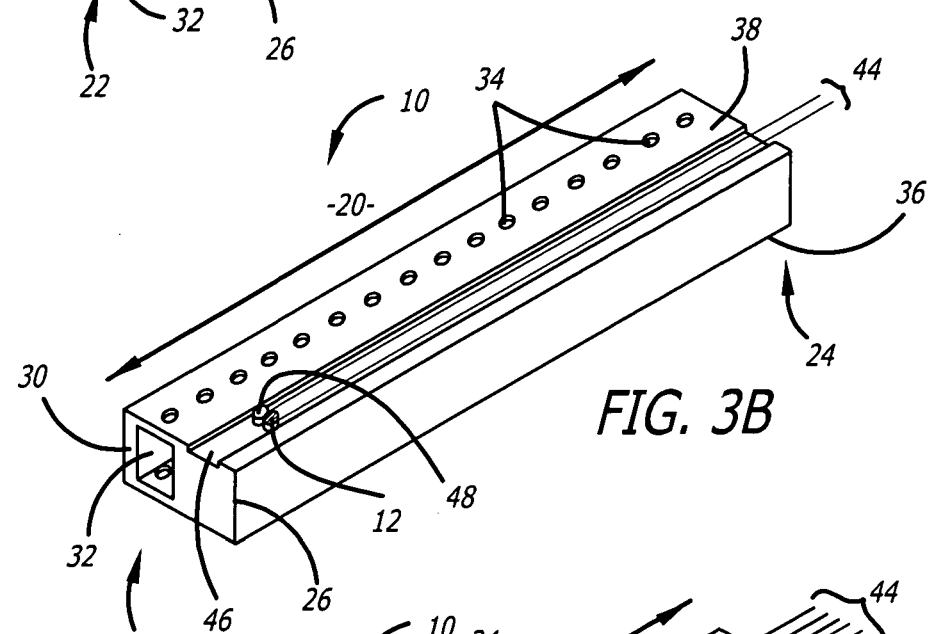

FIG. 3B depicts a bottom view of one embodiment of a surgical drain 10 including at least one sensor 12 positioned in a groove 46 formed in the surgical drain wall 30. The surgical drain 10 may further include a transmitting element 48, and/or at least one or a plurality of drain holes 34 along the drain length 20.

Figure 3C:
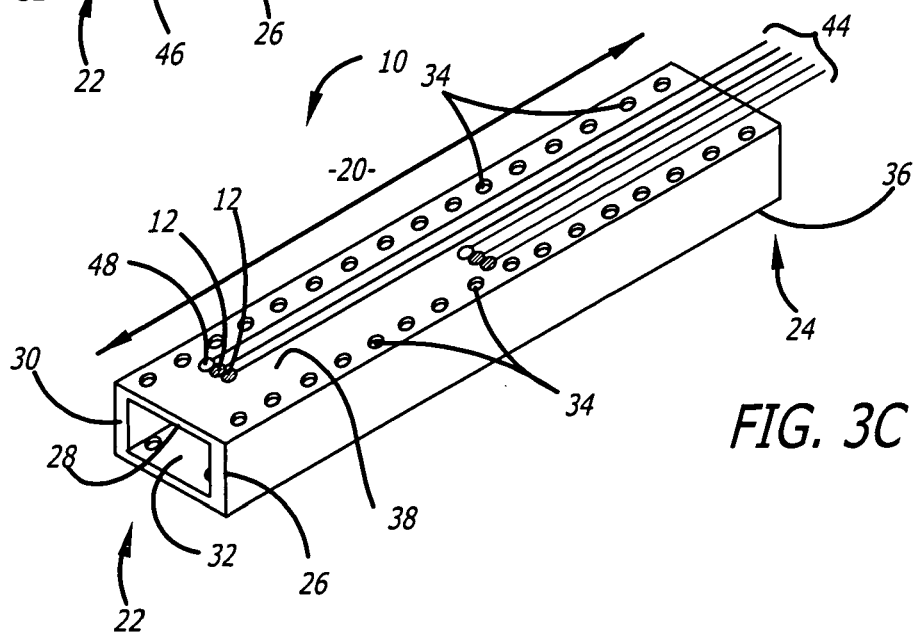

FIG. 3C depicts a bottom view of one embodiment of a surgical drain 10 including at least two sensors 12a/b, spaced at a distance from a transmitter 48 on the drain lower surface 38. In one embodiment, the configuration may be used such that at least one transmitter 48 transmits energy and the sensors 12a/b receive derivative energy to detect different physiological parameters of the tissue 100, such as perfusion, oxygenation and temperature. The configuration may be used to measure the same parameter, and may permit the measurement of energy attenuation over distance between the transmitter 48 and the sensors 12a/b.

Figure 3D:
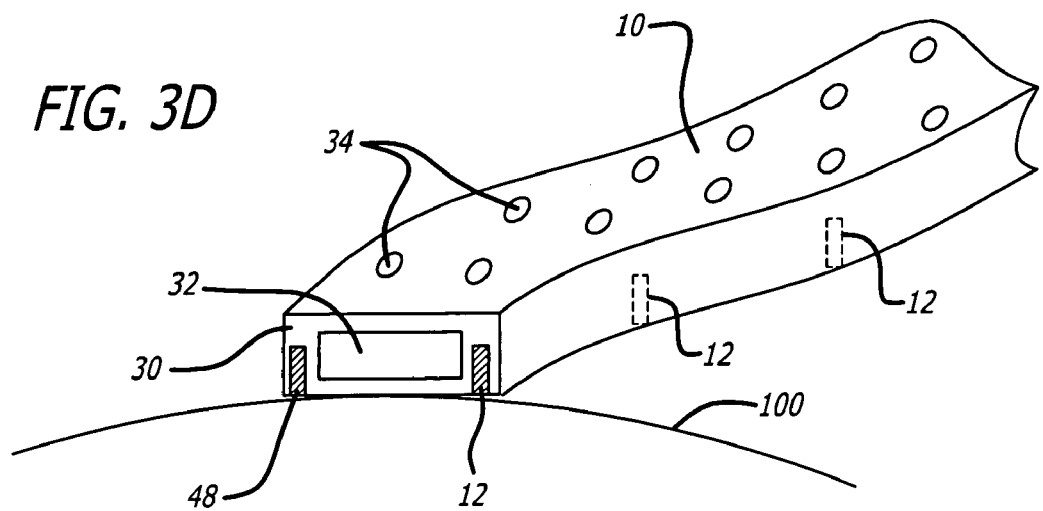

FIG. 3D depicts an end view of one embodiment of a surgical drain 10 including at least one sensor 12 positioned within the drain wall 30. This configuration may allow the positioning of longer sensors in the drain wall and may avoid the need for thicker drain walls. In addition, this configuration may allow a farther placement of a sensor 12 from a transmitter 48 to avoid saturation. This may be a particularly useful arrangement when using high output (e.g., luminance) transmitters for deeper range detection. Positioning of sensors 12 in different areas of the drain wall 30 may permit the collection of information from a variety of tissue locations 100. Information from each location may be compared to obtain differential parameter measures.

Figure 3E:
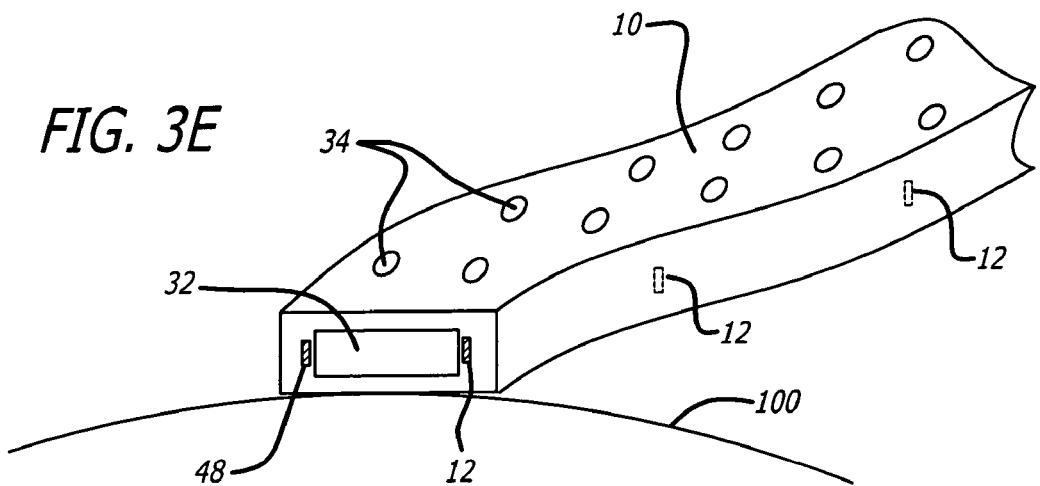

FIG. 3E depicts one embodiment of the surgical drain 10 which may include at least a pair, including a transmitting element 48 and a sensor 12 positioned at different positions of the drain wall 30, such as within approximately opposite sides of the drain lumen 32. In one embodiment, the transmitting element 48/sensor 12 pair may act as an in situ spectrophotometer to detect substances within the drain lumen 32 between the transmitting element 48/sensor 12. Variation of the composition of fluid along sequential pairs of sensors 12 along the drain length 20 may yield information about the source or condition of the fluid. For example, the wavelength dependent attenuation of transmitted radiation by the fluid flowing in the drain lumen may be used to determine whether blood, puss, bile, intestinal contents, and/or a mixture of all are present, according to standard spectrophotometric techniques. The contents of the drain lumen may be is indicative of the condition, including the healing progress of the tissue.

Figure 3F:
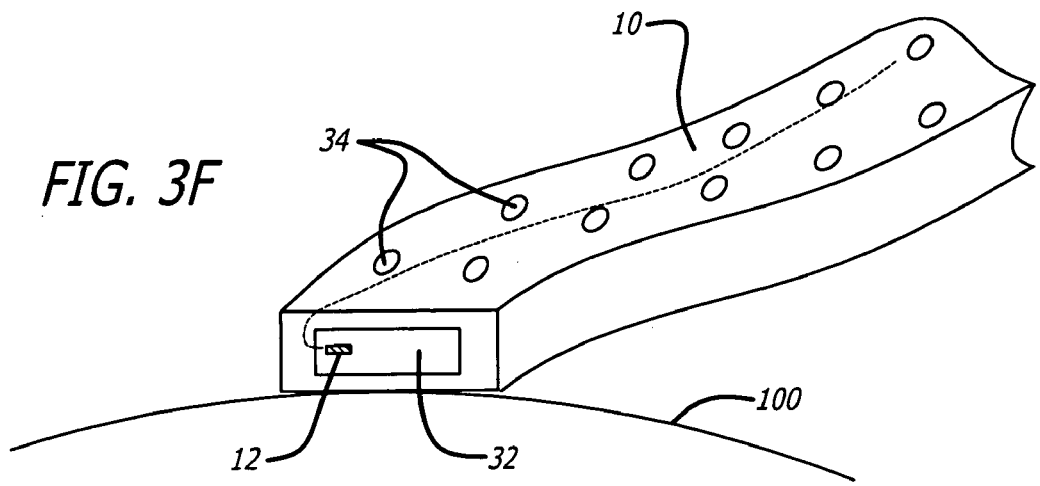

FIG. 3F depicts one embodiment of the surgical drain 10, which may include at least one sensor 12 positioned at least partly within the drain lumen 32. In one embodiment, the sensor 12 may act to detect the composition or the mechanical properties of fluid flowing in the surgical drain lumen 32.

Figure 4A:
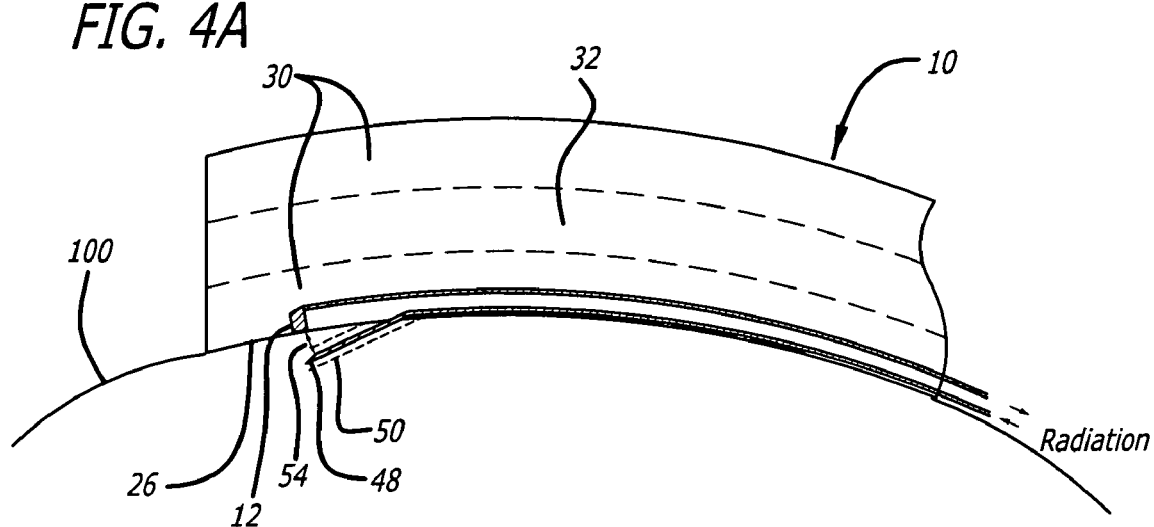
FIGS. 4A & B are schematic diagrams each of a side view of one embodiment of a surgical drain.

FIG. 4A is a schematic diagram depicting a side view of one embodiment of a surgical drain 10, which may include a sensor 12 embedded in the drain wall 30 and a transmitting element 48 to be inserted into the organ 100. The sensor 12 and transmitting element 48 may be fiberoptic or electrical, and the distal ends of each may be oriented such that energy emitted from the transmitting element 48 may be substantially received by the sensor 12. For example, as shown in FIG. 4A the sensor distal end 12 may terminate at a perpendicular to the surgical drain outer surface 26 and the transmitting element distal end 48 may be angled such that the sensor receives energy emitted from the transmitting element 48 distal end. In one embodiment, the distal end of the sensor 12 and the transmitting element 48 may be coaxially aligned. In one embodiment, the surgical drain 10 may include a transmitting element 48 embedded in the drain wall 30, and a sensor 12 to be inserted into the organ 100. In one embodiment, a housing 50 with a housing lumen 52 may be opposed to or encompass the transmitting element 48 or sensor 12 that is being inserted into the organ 100 to provide structural support. The housing 50 with a housing lumen 52 may be a hollow needle made of a biologically compatible material. The housing 50 may advantageously serve as an anchor to attach and/or immobilize the surgical drain 10 relative to an organ 100.

Figure 4B:
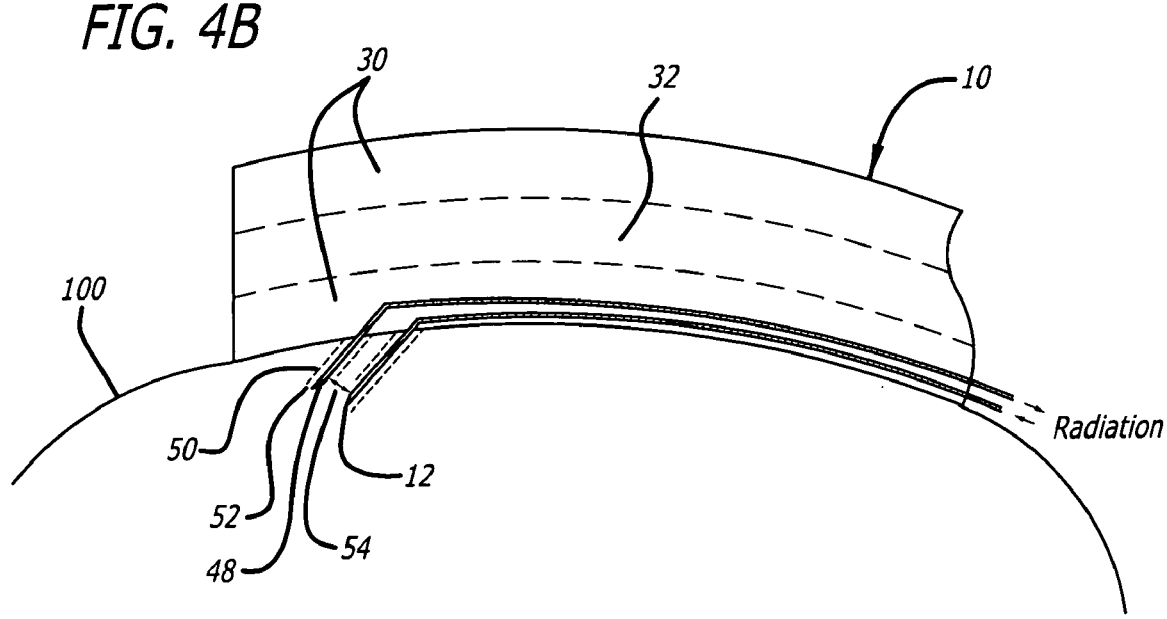

FIG. 4B is a schematic diagram depicting a side view of one embodiment of the invention, which may include optical transmission sensors composed of two needle shaped fiberoptics 12/48 for insertion into a monitored tissue 100. For example, as shown in FIG. 4B the transmitting element distal end 48 and sensor distal end 12 may be angled such that the sensor 12 receives radiation emitted from the transmitting element 48. In one embodiment, the transmitting element 48 and sensor 12 may each be opposed to or encompassed by a housing 50 with a housing lumen 52 to provide structural support. The housing 50 with a housing lumen 52 may be a hollow needle made of a biologically compatible material. The housing 50 can advantageously serve as an anchor to attach and immobilize the drain 10 on the organ 100.

Figure 16:
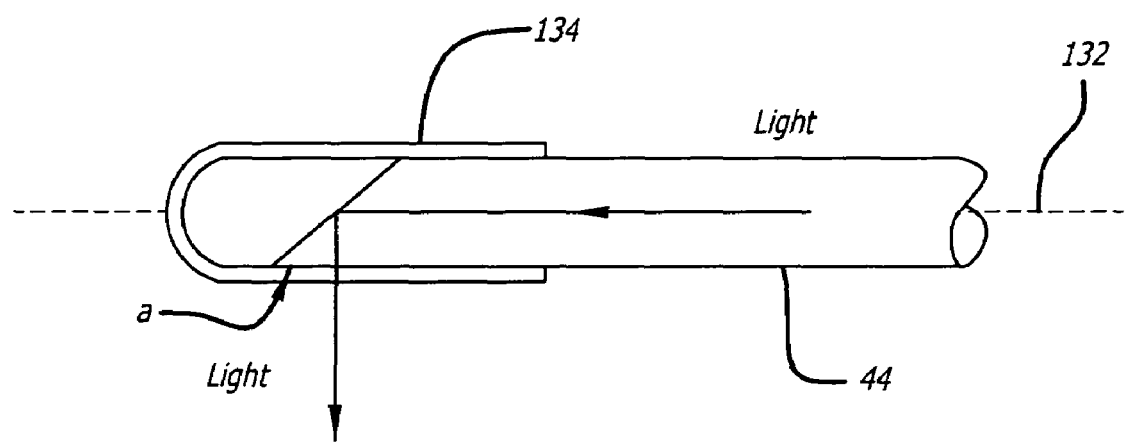
FIG. 16 is a modified distal end of a fiber collecting or receiving energy of one embodiment of a surgical drain.

As shown in FIG. 16, in one embodiment, to enable a fiber to irradiate energy at about 90 degrees, the fiber distal end may be polished at about a 42-degree angle (α) to its axis. Further, glass ferrule caps may be placed over the polished end. In use, the light may be reflected on the polished end, and be emitted at about 90 degrees to the fiber axis 132.

In one embodiment, a fiber collecting or receiving energy may be prepared using a similar process.

In these configurations, for example, light emitted from a transmitting element 48 may be transmitted through a tissue thickness 54 to a sensor 12. Using standard transmission, reflection and/or fluorescence spectroscopy techniques, the transmitted light may be used to measure physiological information including, but not limited to tissue oxygenation, perfusion, coloration, and drug concentration.

FIGS. 5A & B are schematic diagrams depicting a top and bottom plan view of one embodiment of a surgical drain 10. Optical fibers and/or the lead wires 44 that may connect the sensors 12 and the transmitters 48 may be evenly distributed along the drain surface lengthwise to prevent the mechanical twisting of the drain wall 30. This may be advantageous at least to maximize contact between the sensors 12 and the tissue 100.

FIG. 5C is a schematic diagram depicting a cross-sectional view of one embodiment of a surgical drain 10. In one embodiment of the invention, the surgical drain 10 may include at least one pair of sensors 12a/b positioned approximately on opposite sides of the drain wall 30. The surgical drain 10 may also include a plurality of pairs of sensors 12a/b, 12c/d, 12e/f positioned at different locations along the drain length to detect information from different positions along the drain length 20, such as shown in FIG. 6A.

FIG. 6A is a schematic diagram of a side view of one embodiment of a surgical drain; and FIG. 6B is a schematic diagram depicting a cross-sectional view of one embodiment of a surgical drain. In one embodiment of the invention, the surgical drain 10 may include at least one pair of sensors 12a/b positioned proximate to different surfaces of the surgical drain 10. The surgical drain 10 may also include a plurality of pairs of sensors 12a/b, 12c/d, 12e/f positioned at different locations along the surgical drain length to detect information from different positions along the drain length 20.

As shown in FIG. 6B, in one embodiment, the surgical drain 10 may have a drain width 56 of about 15 mm, and a drain height 58 of about 6 mm, a drain length 20 of about 200 mm, a drain hole diameter 34 of about 1.5 mm, and a drain lumen height and width of about 4 mm. The surgical drain 10 may include a plurality of lumens 32; and fibers/wires 44 to and/or from the transmitting elements 48 and/or sensors 12 may be oriented within the surgical drain 10, such as in an internal rib 128. In one embodiment, a sensor 12 may be embedded in the drain wall 30. This may be advantageous at least in facilitating the use of additional modifications to drain wall 30 or outer surface 26, such as stabilization devices and mechanisms for increasing contact between tissue and sensors, described below.

Figure 7:
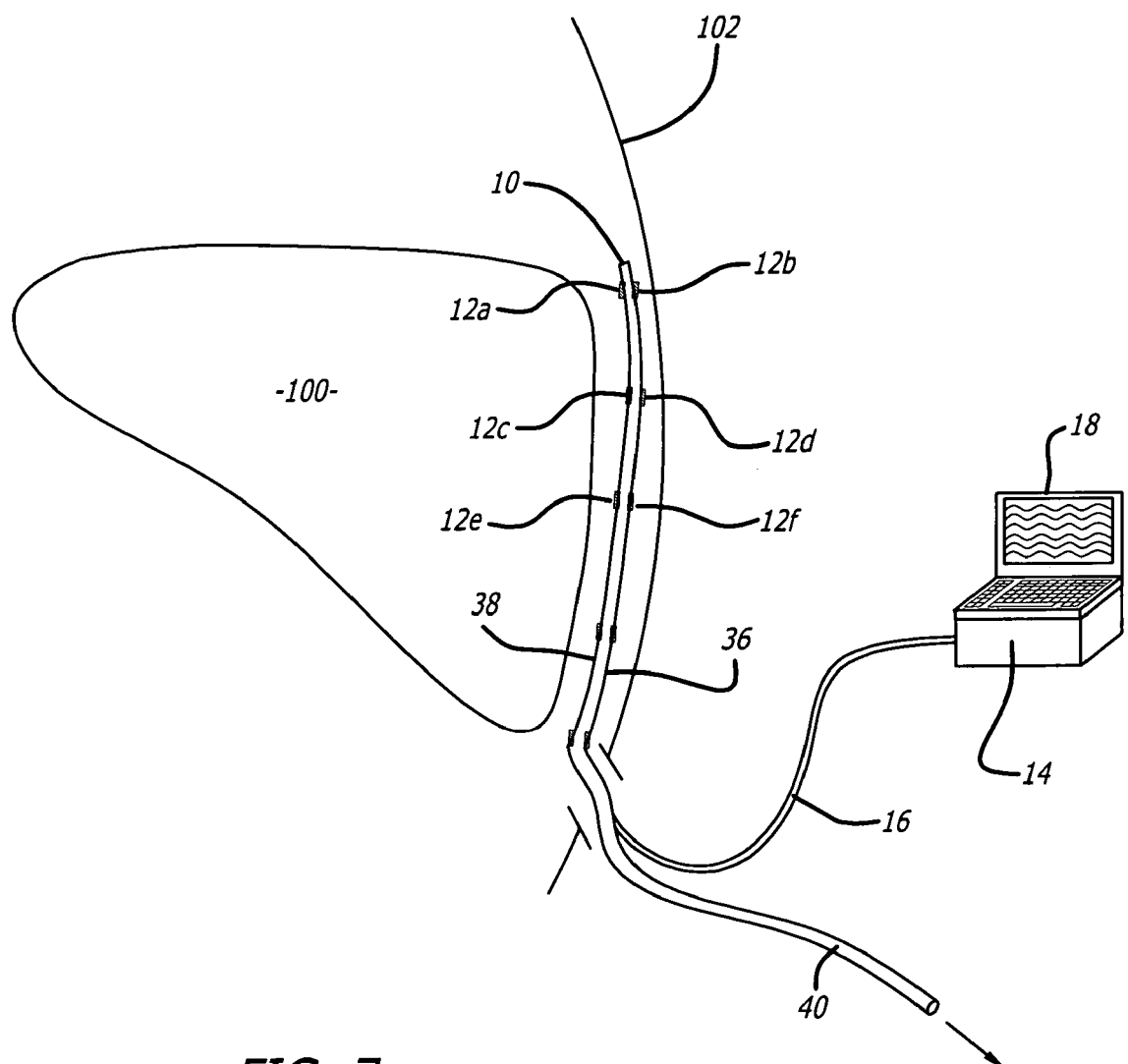
FIG. 7 is a schematic diagram of one embodiment of a surgical drain in use.

FIG. 7 is a schematic diagram depicting one embodiment of a drain in use. In one embodiment, sensors 12 may be placed on opposite sides or proximate to sides of the surgical drain 10 such that the sensor pairs 12a/b may be used to acquire differential measurements between different organs/tissues positioned in the proximity of sensors pair 12a/b. For example, as shown FIG. 7 a surgical drain 10 may be positioned, such that the drain lower surface 38 is proximate to an organ to be monitored 100, and the drain upper surface 36 is proximate to an adjacent tissue. Therefore, sensor pairs 12a/b may be positioned to measure a parameter differentially between the monitored organ 100 and the adjacent tissue. These differential measurements may improve the accuracy of the measurements/diagnosis, such as in monitoring for complications in hepatic perfusion. For example, a lower than normal oxygenation of the liver may not be indicative of problems in the hepatic perfusion because the oxygenation of the whole body may be lower than normal due to respiratory and/or circulatory problems. However, if the oxygenation levels of the liver are lower than normal while the adjacent tissues are at normal oxygenation levels, then this is a real indication of reduced hepatic perfusion.

Any type of sensors (such as oxygenation, perfusion, pH, temperature, color) may be used in a differential mode measurement, such as described above. The sensor 12 type used may be selected so as to maximize the detection of the desired physiological parameter, maximize biological compatibility with the patient's tissues or other components of the device, and to minimize any risk of electrocution or the like.

In one embodiment, the device may be configured to detect the color of an organ 100. The surgical drain 10 may use a single fiber, or may include at least one transmitting element 48 and at least one sensor 12. The transmitting element 48 may be a fiberoptic 44 having a distal end configured to deliver light from a light source to the organ 100. The light may be reflected from, diffusely reflected from or transmitted through at least a portion of the organ 100 in the proximity of the transmitting element distal end 48. The sensor 12 may be a fiberoptic 44 having a distal end configured to collect light having a spectral pattern reflected, diffusely reflected or transmitted through the organ 100, and transmit the spectral pattern to a photodetector or processing system 80. The color may be extracted from a wavelength spectrum using standard wavelength to RGB conversion techniques.

The oxygenation of an organ may be determined by measuring the oxygenation of the hemoglobin within a tissue. The spectral characteristics of hemoglobin are dependent on its state of oxygenation. The oxygenation of the organ 100 may be determined by measuring the spectral characteristics of hemoglobin using a similar sensor 12, as described above.

The monitoring system 14 may include a processing system 80 for converting the spectral pattern information to a color, which may be presented to a physician on a display 18. The processing system 80 may also convert the spectral pattern information to a color index number, which may be presented to a physician on a display 18. The system may also include data of normal colors and color indexes for automatic or manual comparison so that a tissue abnormality may be noted.

Determining the physiological conditions, such as color and/or color index of the tissue, may be advantageous at least in that the physician may determine from the color of the tissue the general health of the tissue, including whether the tissue is adequately oxygenated and/or jaundiced. Further, the monitoring function is advantageous in that it may be continuous or at intervals selected. Further, the monitoring function is advantageous in that is may be minimally invasive and does not require opening the patient to assess the tissue condition.

In one embodiment, diffuse reflection may be used to determine the oxygenation level of at least a portion of an organ 100. This method may be advantageous at least in that information about the internal portion of the organ 100 may be obtained, without penetrating the surface of the tissue with a sensor 12 or a transmitting element 48.

In one embodiment, the device may be configured to detect the temperature of the monitored organ 100. In one embodiment, the device may include a fiberoptic temperature sensor as described above in proximity to the surgical drain 10. The temperature sensor 12 may transmit the light for information processing. A processing system 80 may convert the phosphorescence decay-time to a temperature value which may be presented to a physician on a display 18. The system may also include data of normal temperatures for automatic or manual comparison so that an abnormality may be noted. Determining the temperature of the organ 100 is advantageous at least in that the physician can determine from the temperature the general health of the tissue including whether the tissue is being properly perfused after transplant as improperly perfused tissues may decrease in temperature, for example. A temperature sensor 12 may be of any type other than fiberoptic including thermistors, thermocouples and resistance temperature detectors (RTD's), for example.

The system may acquire simultaneous differential measurements from along the drain length or between the different tissues between which the surgical drain 10 is positioned. Measurement of a given parameter simultaneously from adjacent normal organs/tissues (e.g., abdominal wall) and from the organ/tissue of interest suffering problems (e.g., the liver) can provide a control or reference value. This control or reference value can be used as a comparison factor to improve the accuracy of the parameter measured from the organ/tissue of interest 100.

In one embodiment, the device may be configured to detect the respiratory coenzyme NADH levels from the monitored organ 100. Fluorescence spectroscopy may be used to measure the fluorescence of NADH which has a peak emission at 470-nm and to detect its concentration in the tissue 100.

In one embodiment, the device may be configured to detect concentrations of exogenous drugs within the tissue 100 or fluid in the drain lumen 32. For example, drugs (such as chemotherapeutic agents) may auto-fluoresce or may be coupled with a fluorescing tag having a selected peak emission, which may be detected by fluorescence spectroscopic methods.

In one embodiment, the device may be configured to detect pressure. In one embodiment, the surgical drain 10 may include fiberoptic pressure sensors as described above.

The surgical drain 10 may include at least one or a plurality of sensors 12 in communication with a monitoring system 14, such as via a data cable 16, such as shown in FIG. 1A. Wires and/or fibers 44 may be bundled together towards the surgical drain 10 proximal end and exit the surgical drain 10 within a sheath.

Figure 8A:
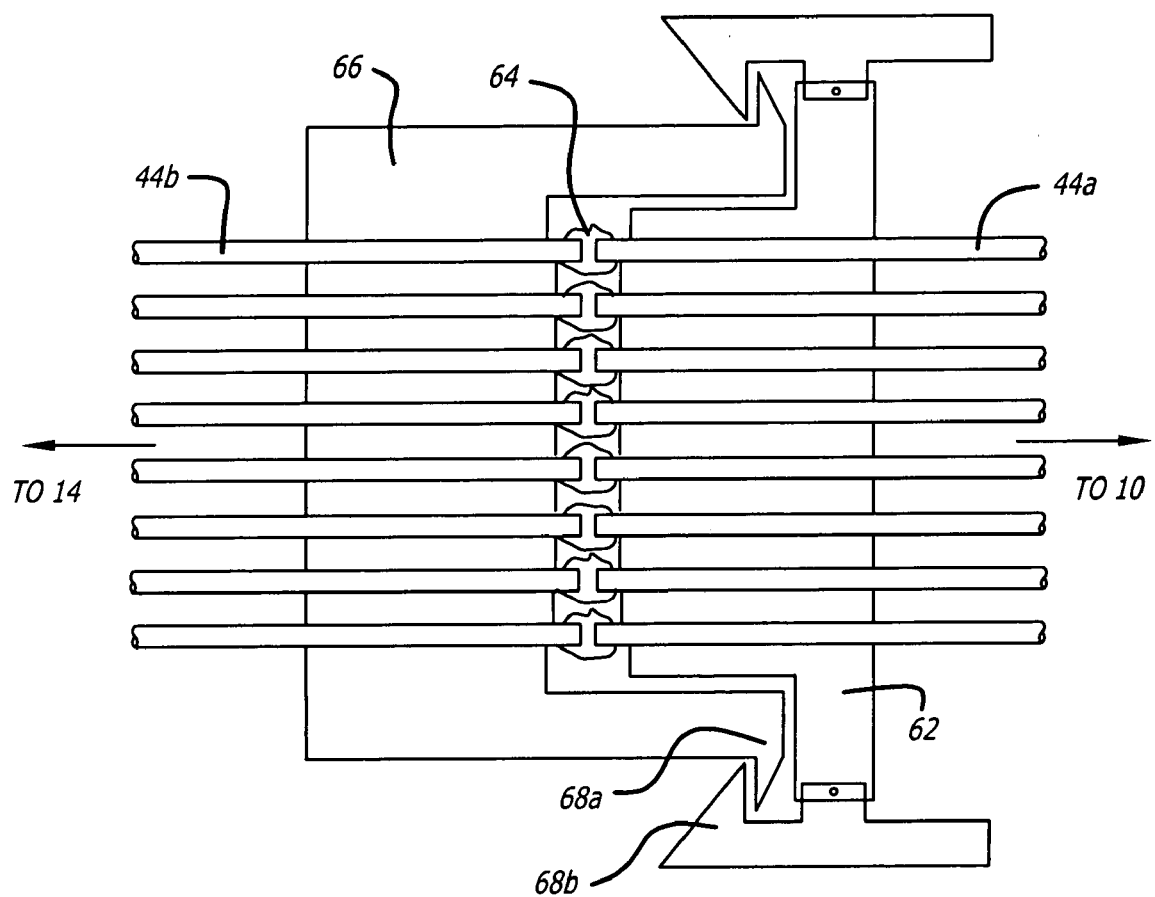
FIGS. 8A & B are a schematic diagrams each of an alternate embodiment of a multifiber connector.

In one embodiment, the surgical drain 10 may include optical fibers 44a/b and a multifiber connector 62 may be an optical fiberoptic connector, which joins each fiber 44a to a complementary fiber 44b in the monitoring system 14 to establish optical continuity. FIG. 8A is a schematic depicting a side view of one embodiment of an optical connector 62 that may be constructed to minimize the distance between the apertures of the corresponding optical fibers 44a/b. The region where the fiber apertures meet may be filled with an index-matching substance 64, such as optical gel to optimize the optical continuity between the corresponding fibers 44a/b. The optical gel may fill the air gap between corresponding optical fibers and hence improve light transmission by decreasing the back reflection that may occur at an air interface due to mismatch in the refractive index. The connector 62 may be configured so as to have a complementary shape to a receptor 66. The connector 62 and receptor 66 may include complementary locking members 68a/b to maximize the meeting of the apertures of the corresponding optical fibers and prevent inadvertent separation between the components.

Figure 8B:
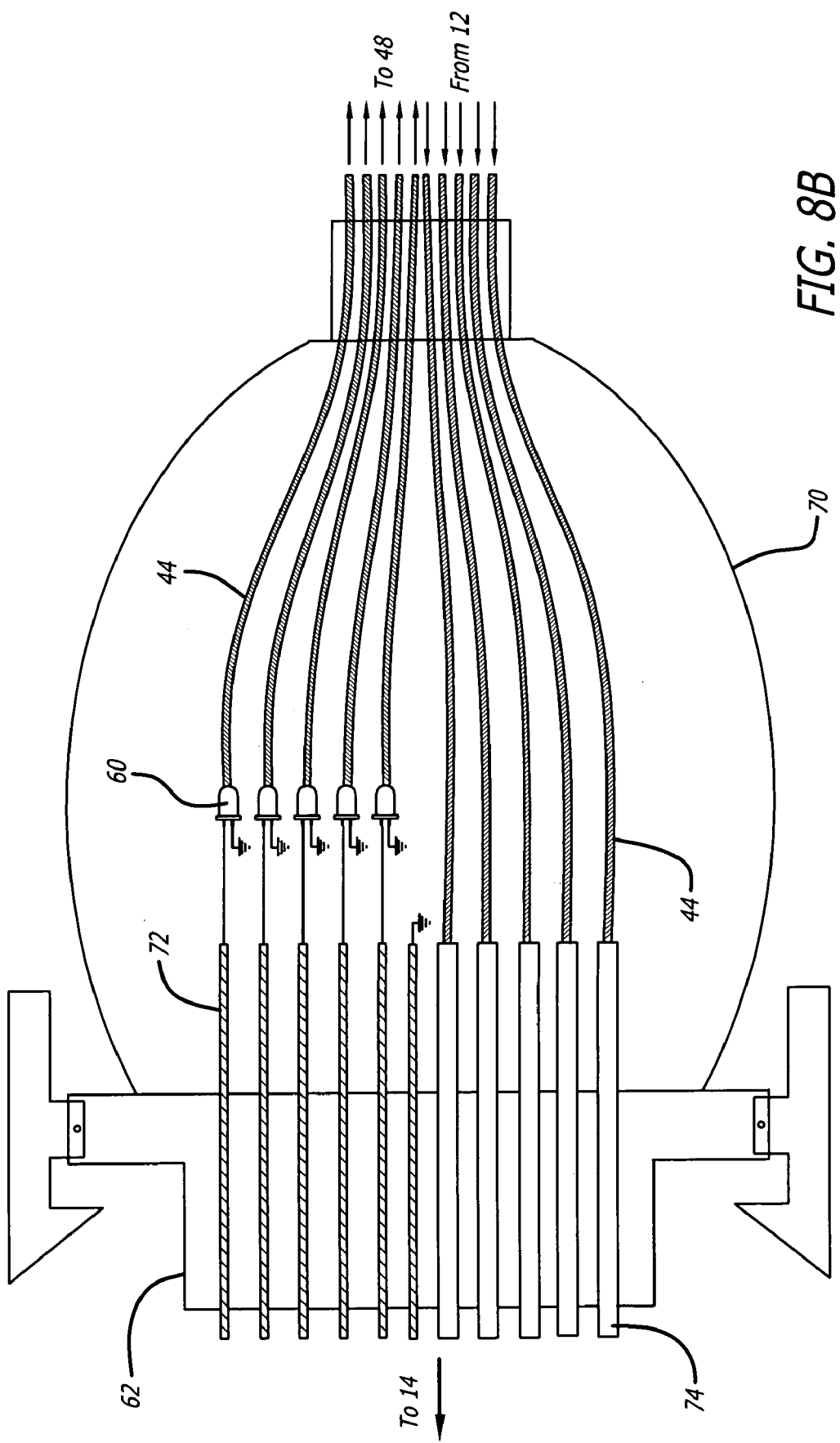

FIG. 8B is a schematic depiction of one embodiment of a multifiber connector 62, which may be used in a surgical drain 10 including light sources 60. In one embodiment, at least one light emitting diode (LED) may be used as a light source 60, such as when low power consumption is desirable. The LED may be of the white, multi-wavelength, or monochromatic type. An LED-block 70, such as shown in FIG. 8, may be used to couple at least one LED to a transmitting element 48, such as an excitation optical fiber 44 and hence minimize light losses at the multifiber optical connector 62. In one embodiment, electrical connectors 72 may be used to drive LEDs 60 in a LED-block 70, while the optical connectors 74 may be used to guide the 54collected optical signals from sensors 12 to a monitoring system 14.

Figure 9:
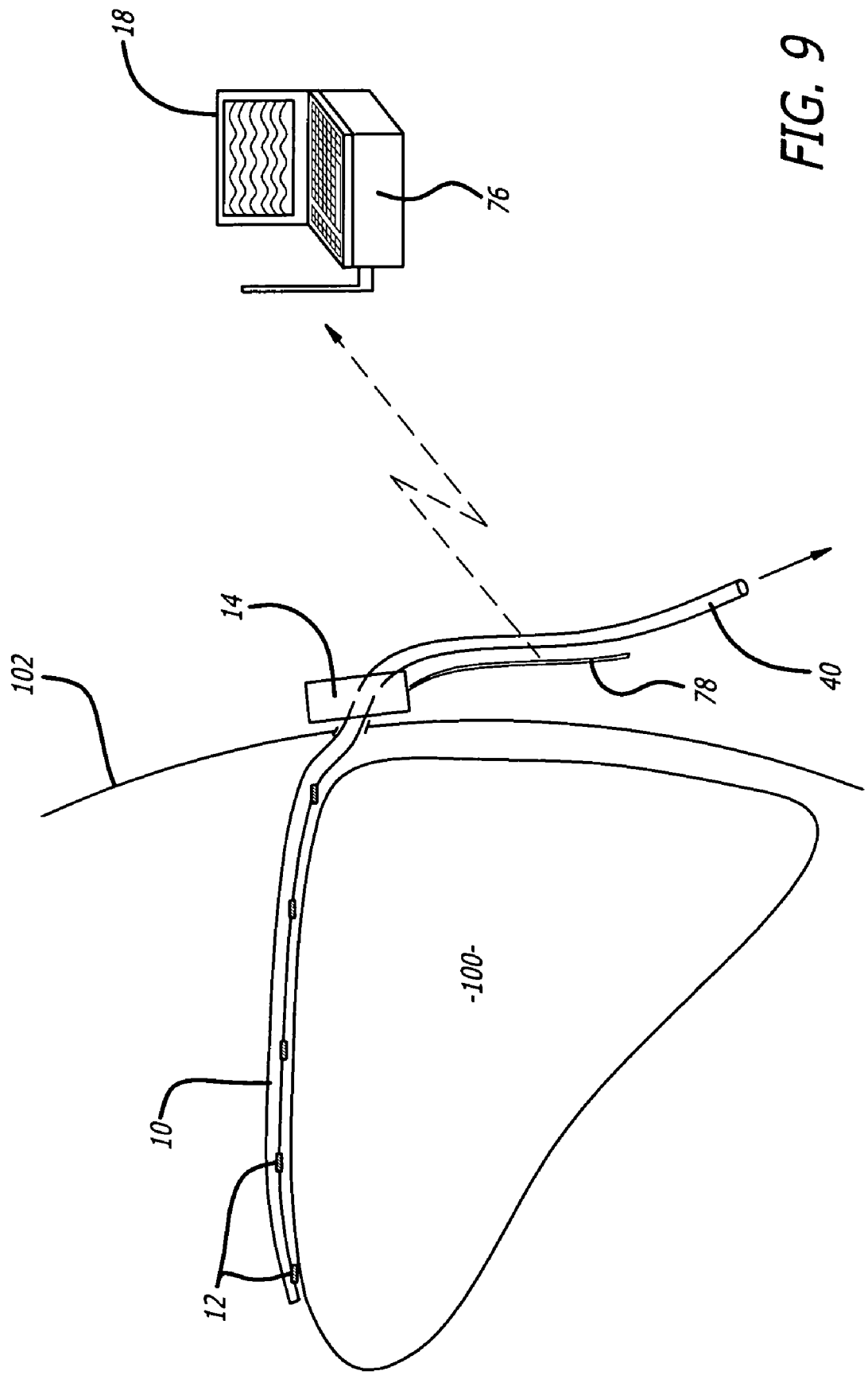
FIG. 9 is a schematic diagram of one embodiment of a surgical drain with wireless connectivity.

FIG. 9 is a schematic diagram depicting one embodiment of a surgical drain with sensors and wireless connectivity. In one embodiment, the device may include a monitor 14 in communication with the sensors 12 of the surgical drain 10. The monitor 12 may be directly affixed to the end of the surgical drain 10 and/or tube 40, and may utilize an antenna 78 to receive command signals to activate transmitting elements 48 and/or transmit data obtained from the sensors 12 to a receiver 76. If the monitoring system 14 includes an antenna 78, the antenna 78 may be positioned such that it runs longitudinally along the drain tube 40.

In one embodiment of the invention, the device may comprise a surgical drain 10 in communication with a monitoring system 14 that may include a processing system 80, a display 18, device(s) to drive the frequency and/or magnitude of signals to transmitting elements (such as a lamp multiplexer 82) and/or receive and detect information from sensors 12 and/or a device to record information from a sensor 12 associated with the surgical drain 10 over time. The monitoring system 14 may be configured so as to continuously obtain information regarding the condition of the organ or obtain information only at preselected intervals or on demand from a physician. In one embodiment of the invention, the monitoring system may include a recorder 108. The recorder 108 may store acquired information for later retrieval and review. The recorder may be a hard disk of a processor or computer. Extended history (e.g., 7 days) of a given physiological parameter may be stored and later retrieved from the recorder, and displayed if desired. The processor 80 may include signal-processing algorithms to automatically detect and alarm for abnormalities. In one embodiment, the system may include an alarm which may be triggered when an abnormality is detected in a physiological parameter is detected (relative to pre-set values) or when inadequate contact of sensors to make a measurement. The system may include a manual preset of the alarm threshold.

In one embodiment of the invention, the processing system 80 may process the reflectance intensities received from the sensing system at about 540, 580 and 640 nm to determine if a reflectance sensor 12 is in optimal contact with an organ 100. FIG. 13G shows one example of the reflectance spectrum of white light from the surface of a deoxygenated liver. Spectrum 200 may result from a reflectance sensor that is in good contact with the surface of the organ 100. Spectra 210, 220 and 230 may result from a sensor 12 that is not in contact with the organ 100. The processing system may activate a pump 118 upon detection of a spectrum representing poor sensing system contact such as 210, 220 and 230 or the like. The processing system 80 may further control a pump 118 to incrementally pump a fluid (e.g., saline) volume into the inflatable chambers 114 while measuring changes in the spectrum after each pumped volume. The filling of the inflatable chambers 114 may push the sensor 12 closer towards the organ 100. The processing system 80 may stop this contact ensure sequence upon the measurement of a spectrum representing optimal sensor contact with the organ 100, such as about spectrum 200, or the like. A pressure sensor 120 may monitor the pressure output from the pump 118 and provide real-time feedback information to the pump 118 and the processing system 80 to avoid excessive pressure that may rupture the inflatable chamber 114. The processing system 80 may memorize the volume pumped into the inflatable chamber 114, so that it can be withdrawn later or repeated at a later time.

The system may be configured to permit a physician to be able to review previously recorded data simultaneously while the monitor 14 is recording. The system may include a search feature, such that a physician may display the data segments where selected physiological information occurs, such as periods where abnormalities were detected (e.g., hypoxia or ischemia). The system may also include an alarm feature, selectable by the user so that the system may alert the user if an abnormality is detected. A display 18 may include a touch-screen graphic user interface 112. For example, the graphic user interface 112 may permit a user to select options, including but not limited to history review of the information detected for a selected parameter, review of abnormal conditions, select alarm option, freeze screen option, trace display option, sample interval selection, display mode. In one embodiment, the physician may select an interval at which measurements are obtained from the tissue. This interval may vary, for example from about 1 to 60 minutes, such as about 5 minutes.

Figure 10:
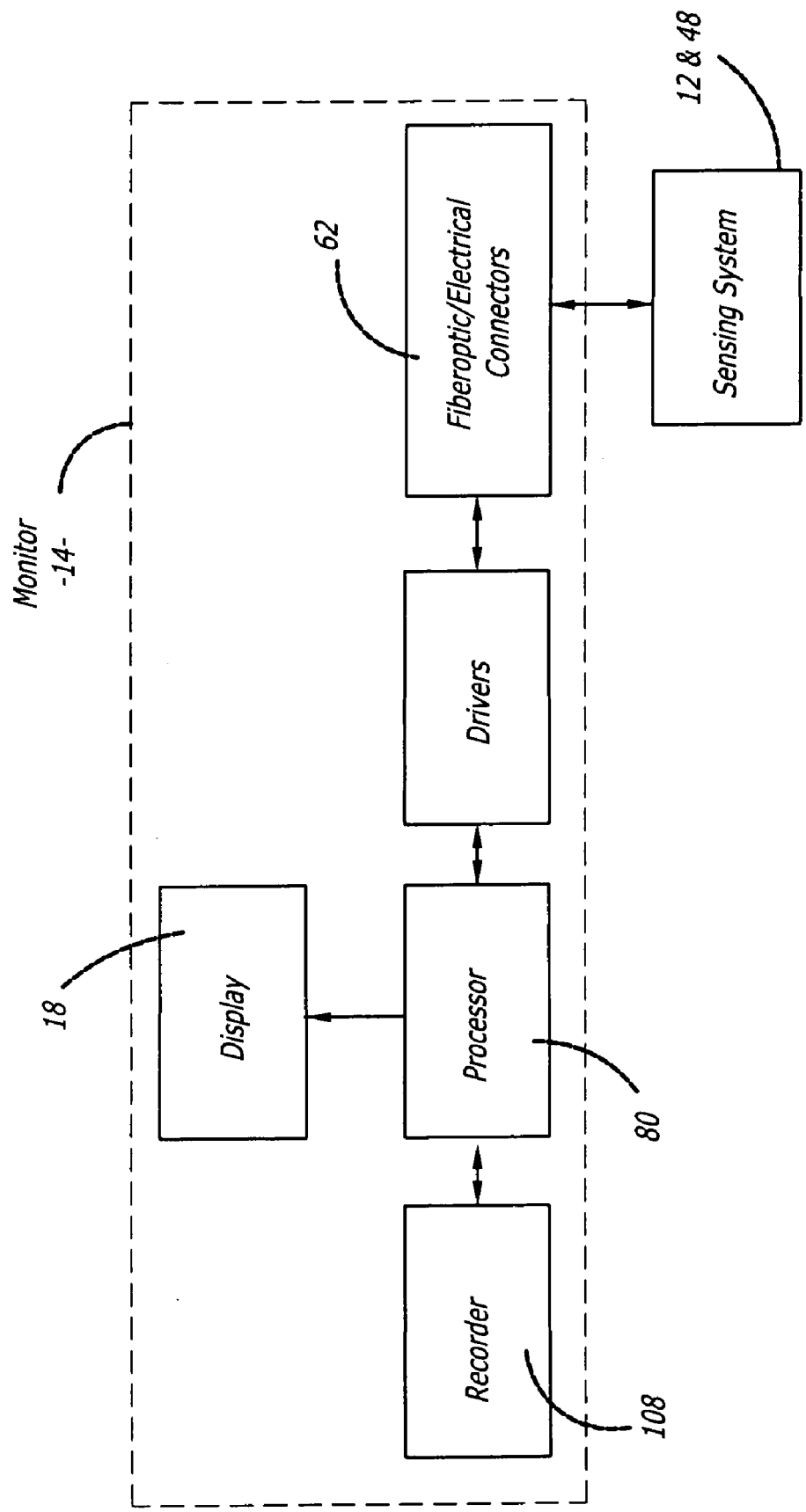
FIG. 10 is a flow diagram of one embodiment of a monitoring system of the invention.

FIG. 10 is a schematic depiction of one embodiment of a monitoring system 14. In one embodiment of the invention, the monitoring system 14 may include a processor 80, a display 18, a fiberoptic thermometer and a spectroscopic system. The spectroscopic system may include a spectrograph and a multiplexed light source, which may be used to measure parameters such as the tissue perfusion, oxygenation and color. The spectrograph, lamp multiplexer 82 and/or thermometer may be connected to a processor 80, such as by computer interface such as universal serial data bus (USB), digital input/output interface card (DIO), analog to digital converter (A/D), and/or RS232 serial port.

In one embodiment, a spectrometer 88 may be used to monitor physiological parameters at a plurality of locations of the organ 100 corresponding to the sensors 12 positioned at various positions along the drain length 20.

Figure 11:
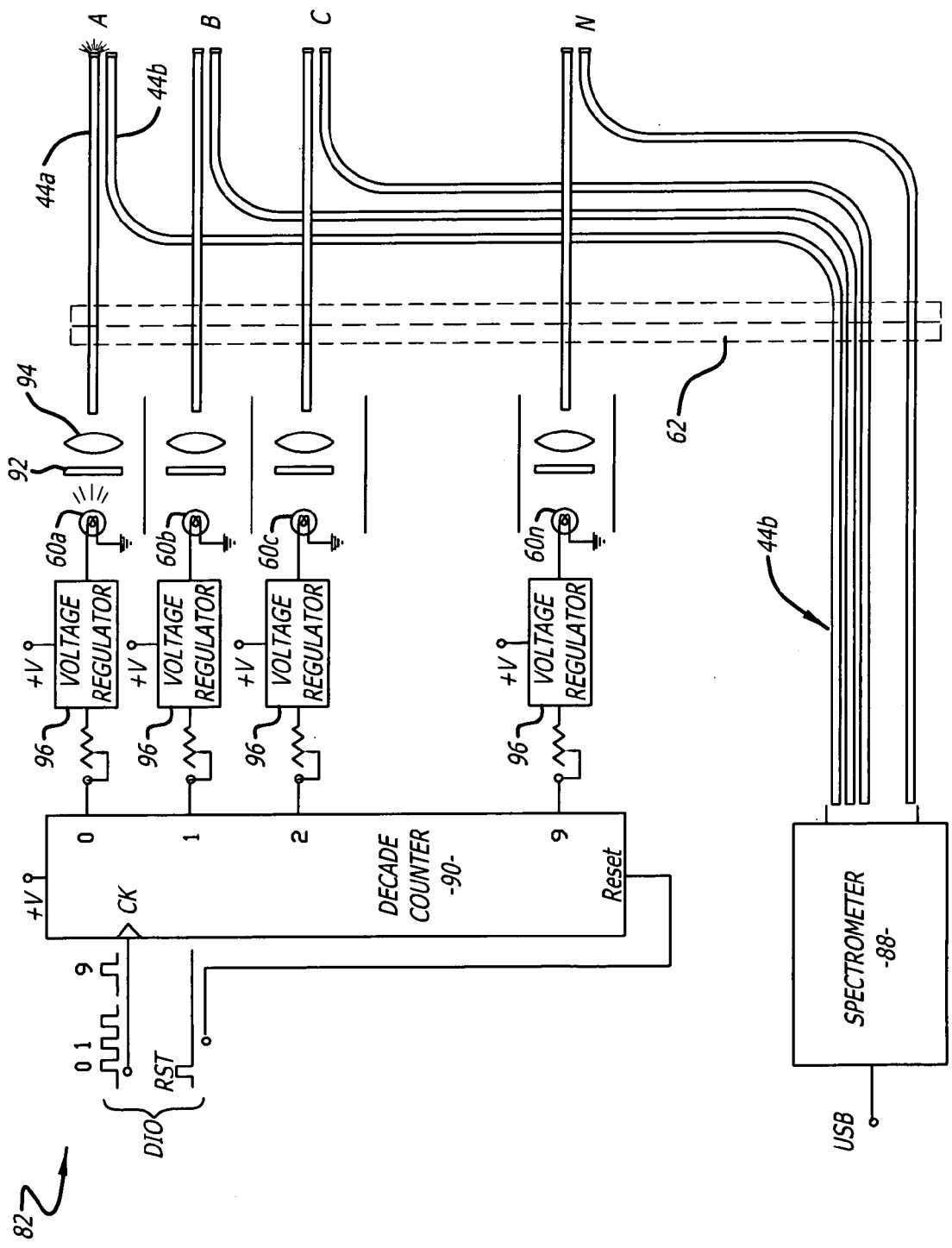
FIG. 11 is a schematic diagram of one embodiment of a multiplexer circuit.

FIG. 11 is a schematic depiction of one embodiment of a lamp multiplexing configuration 82. An excitation optical fiber 44a may transmit light from a lamp 60 to a tissue 100, while a collection optical fiber 44b may collect light reflected from, diffusely reflected from or transmitted through the tissue 100. The system may be configured such that light is emitted from one lamp 60a for transition via an excitation optical fiber 44a terminating at a first position (A) of the organ 100 for a selected duration of time, at which time no other lamp (such as 60b or 60c) emits light at a second (B) or third (C) position of the organ 100 (as shown in FIG. 2A). A counter 90 may be controlled by two signal lines (i.e., clock and rest) to multiplex the spectral acquisition from different locations relative to a tissue. In one embodiment, a plurality of optical collection fibers 44b may connect to the spectrometer 88, while each of the excitation optical fibers 44a may receive light from a separate lamp 60a-c, respectively. Hence, the spectrometer 88 may measure the spectrum of the light received via any of the plurality of collection fibers 44b at a selected time. In use, a sensor 12 may be in the dark (i.e., inside the body) and cross talk minimized between sensors 12, such as by positioning the sensors at a suitable distance from one another along the drain length 20.

With respect to the lamp 60, an optical filter 92 may be used to remove undesired wavelength bands such as those in the ultraviolet region. A lens 94 may be used to focus light emitted by a lamp 60 into the proximal aperture of the optical fiber 44a. An adjustable iris (not shown) may be used to limit the light intensity to the desired levels. A voltage regulator 96 may used to supply a constant voltage to the lamp 60 and hence maintain constant irradiation levels. The processor 80 or a separate drive may control the light on/off via its interface with the multiplexer 82.

In one embodiment, a measured spectrum of the light (such as diffusely reflected) may be corrected for distortions caused by the dark current, ambient light and/or spectral response of the system. The spectra measured by a spectrometer 88 may be processed by the processor 80 according to the known methods of diffuse reflectance spectroscopy (or transmission spectroscopy methods if applicable) for the measurement of the concentrations of oxygenated and deoxygenated hemoglobin in an organ 100. The spectral classification methods may include peak ratios, artificial neural networks (ANN), multiple linear regression (MLR), principal component regression (PCR), and partial least squares techniques (PLS).

In one embodiment, standard methods for converting wavelength to visual red, green, blue ("RGB") may be used to regenerate a color corresponding to the spectra collected from the organ 100 for visualization on a display 18 of the monitoring system 14. The wavelength to color transformation formula and the color display algorithm values may be calibrated using colorimetry techniques to ensure that the displayed color is visually similar to the actual color of the organ 100.

In one embodiment, spectral information obtained regarding the organ 100 may be converted to a color index, such as a number for visualization on a display 18 of the monitoring system 14. A numerical color index may be displayed to provide the physician with a quantitative color evaluation of the organ 100. This may be advantageous at least in diagnosing tissue conditions, which affect the color of the organ 100, such as jaundice and ischemia.

Figure 12A:
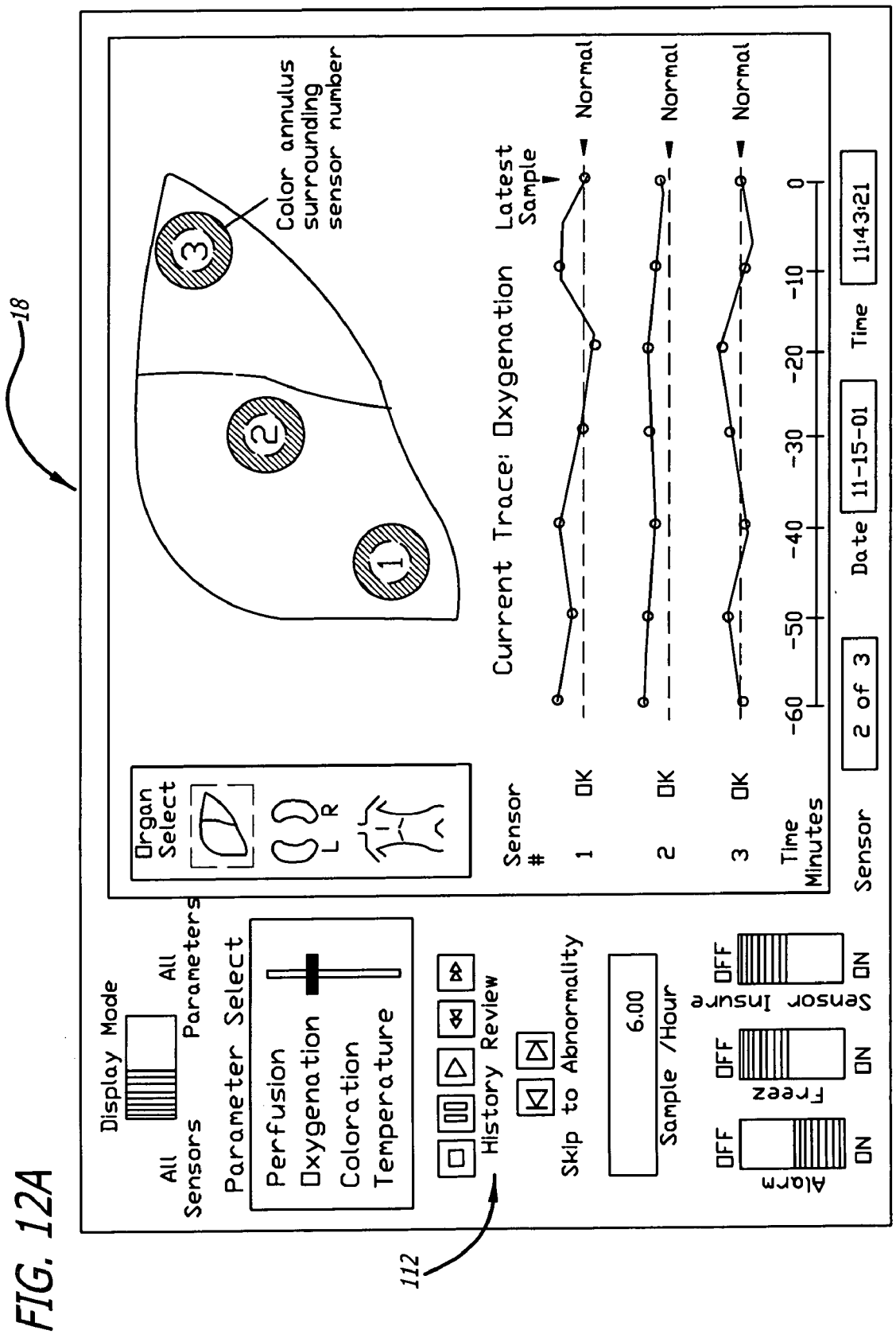
FIGS. 12A-E are schematic diagrams each depicting one embodiment of a display.
Figure 12B:
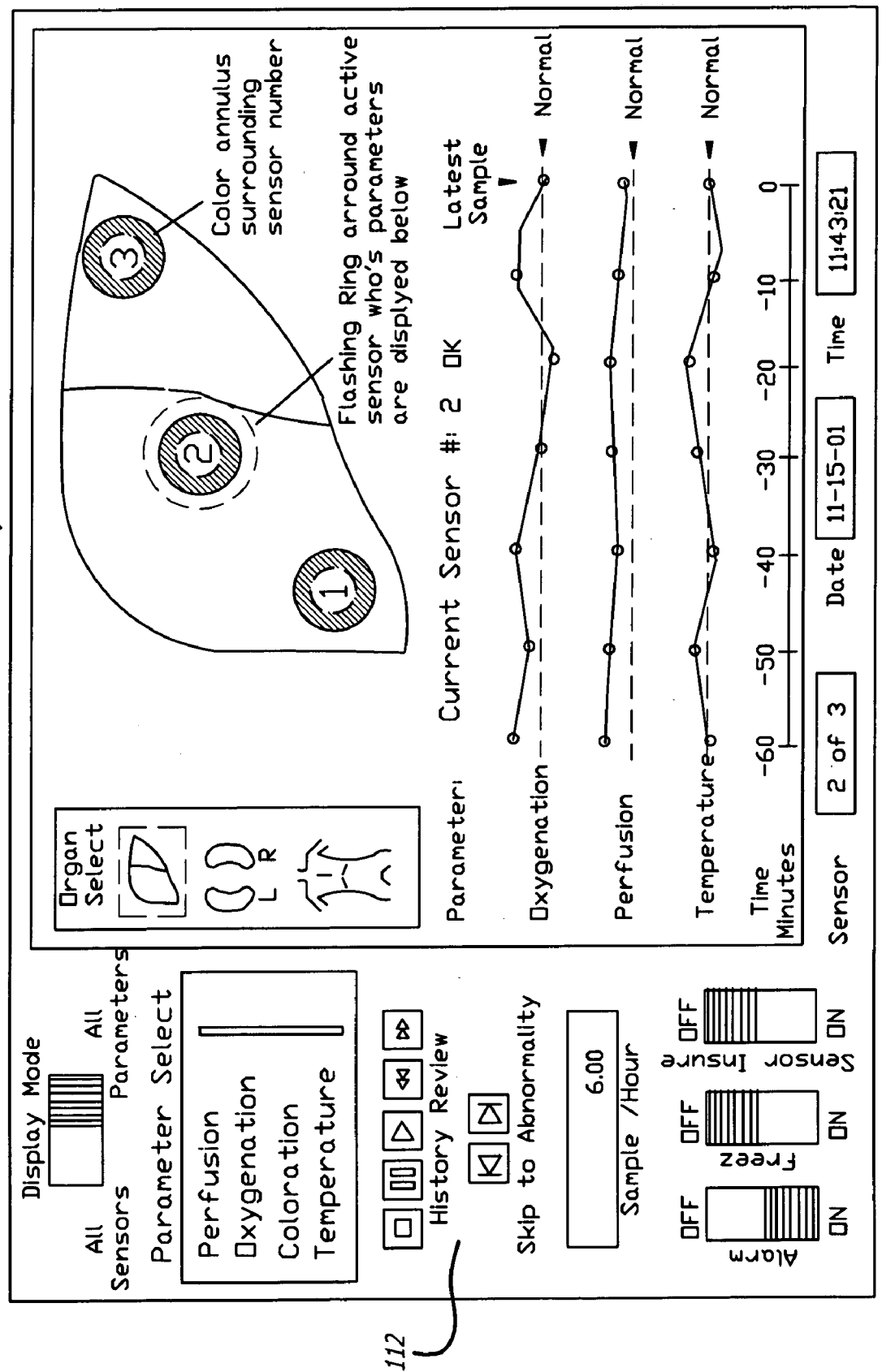

A display 18 may show information, for example in a graphical, numerical or color form to a physician of user-selected physiological parameters including, but not limited to, tissue oxygenation, perfusion, temperature, coloration, pH and pressure. FIGS. 12A-E are schematic diagrams depicting one embodiment of a display 18. In FIG. 12A, for example, the display 18 may include a screen showing at least one selected parameter for each sensor position on the organ 100 (such as "1," "2" or "3") over a selected time. In this example, oxygenation levels are shown graphically over time, and corresponding patches of color are depicted on a graphical symbol of the selected organ relative to the position of each sensor 12 along the organ 100. The color patch may be depicted as an annulus surrounding the sensor number from which the color is detected. In FIG. 12B, for example, the display 18 may include a screen showing a plurality of different parameters for a single sensor position upon the organ 100 over a selected time. In this example, oxygenation, perfusion and temperature levels are shown graphically over time, and the corresponding patch of color is depicted on a graphical symbol of the selected organ relative to the sensor 12 (e.g., "2") for which the information is being displayed. The color patch may be depicted as an annulus surrounding the sensor number from which the color is detected. A screen indicator may mark the sensor number from which the displayed oxygenation, perfusion and temperature values were collected. The operator may select to display the parameters set of any sensor by simply clicking on the symbol of that sensor on the touch screen.

The physiological parameter detected by each sensor 12 (such as perfusion or oxygenation of the tissue at the location of each sensor) may be visualized on a display 18 as percentage of predetermined normal values. For example, the display 18 shown in FIG. 12C displays the oxygenation traces of five sensors along the drain length 20 relative to a normal value.

Figure 12C:
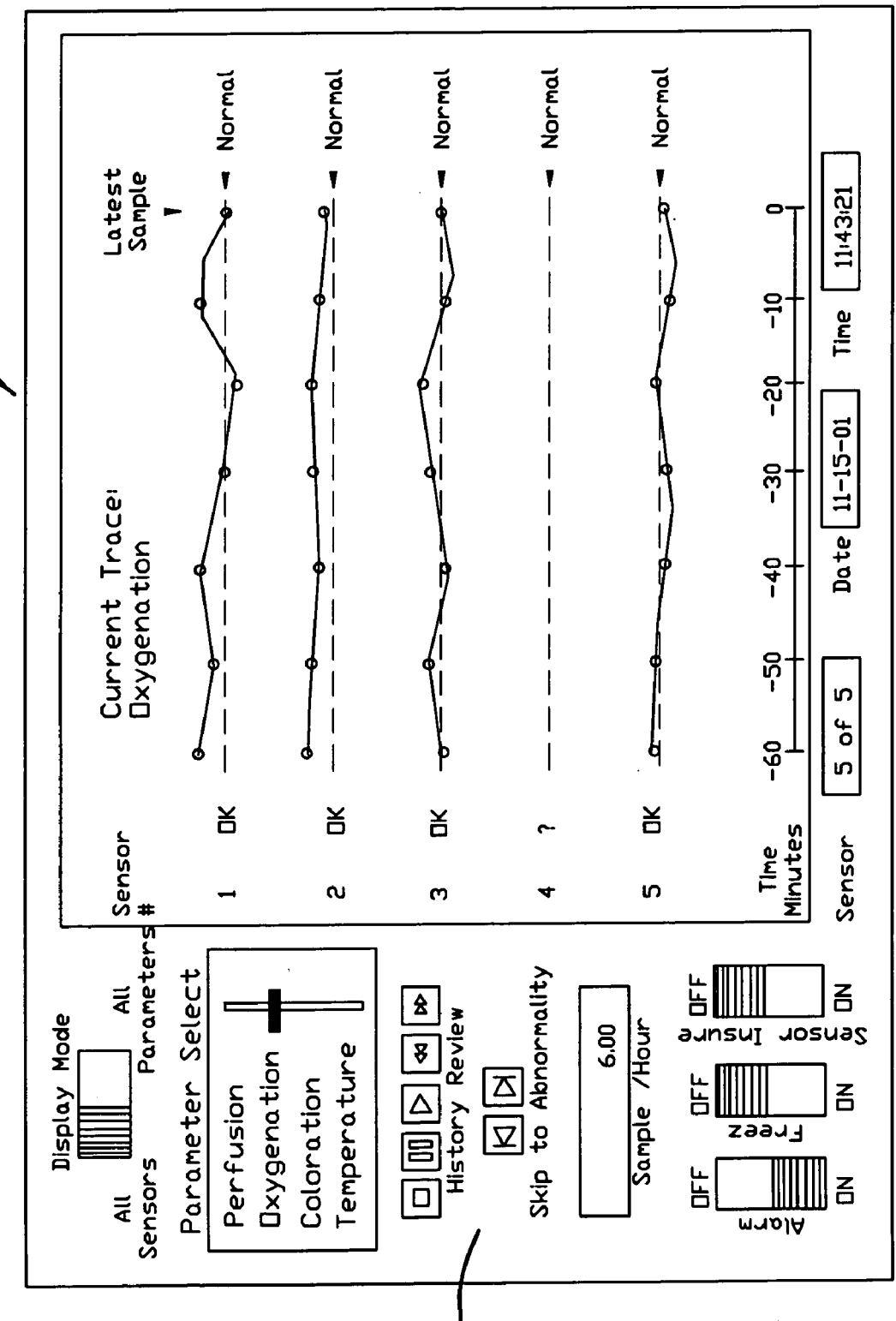

FIG. 12C is a schematic depiction of one embodiment of a display 18. A physician may select to display at least one of selected physiological parameters such as tissue perfusion, oxygenation, color or temperature at each trace representative of each sensors, as shown in FIG. 12C. The display may also indicate if a sensor is not operating to collect information (such as in trace "4"). The display may include a user input such as "Sensor Ensure" button which when activated employs the "sensor contact ensurance system" shown in FIG. 13, if needed. The user may select this feature to ensure that all sensors are in good contact with tissue 100, where and when needed.

Figure 12D:
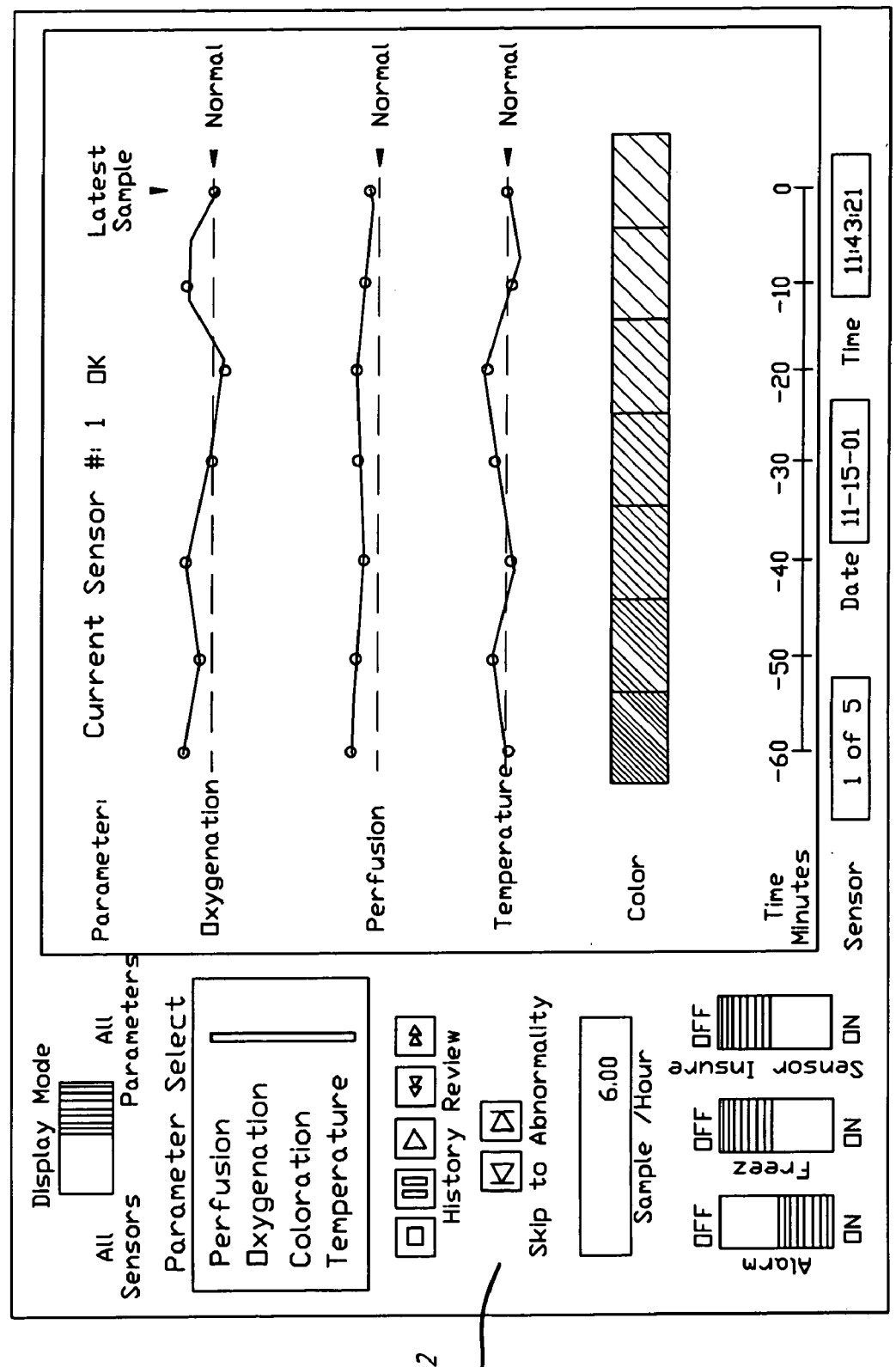

FIG. 12D is a schematic depiction of one embodiment of a display 18. In one embodiment, the physician may select to display different physiological parameters measured at each sensor location, as shown in FIG. 12D. The display 18 may be configured such that multiple screen windows may be opened to display different sensor locations at the same time.

Figure 12E:
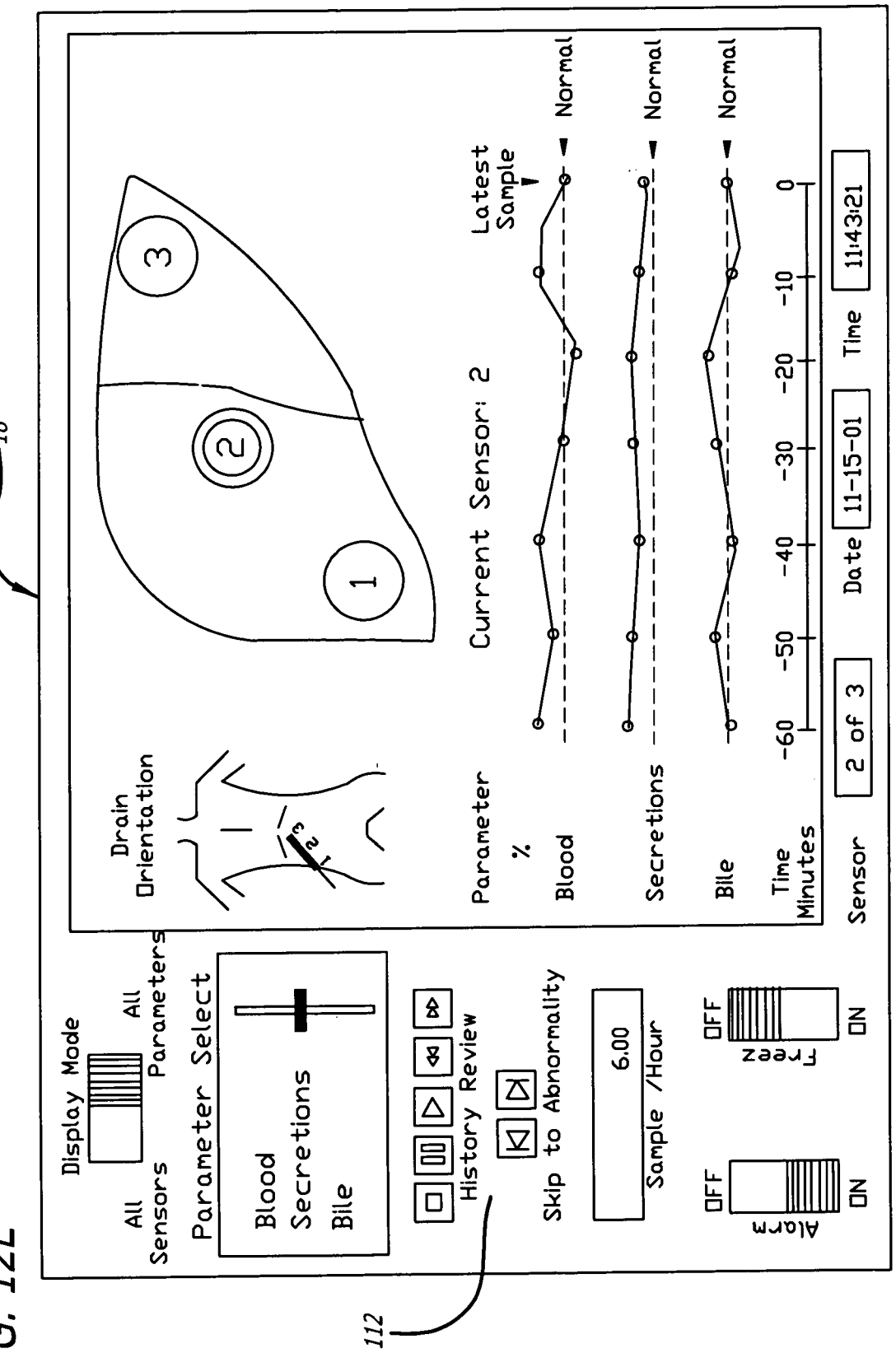

FIG. 12E is a schematic depiction of one embodiment of a display 18. As shown in FIG. 12 E, measured parameters include: blood content, abdominal secretions and bile. These parameters may be measured optically using standard spectrophotometric techniques. Other optical and electrical sensors may be used to measure the pH and the concentration of ions in the drained fluid, for example.

As depicted in this example, the surgical drain has three optical sensors distributed along the drain length 20 for detecting fluid within the lumen at each of the locations. Using the "Display-Mode" slide button, a user may select to display all the parameters at a given sensor location or a single parameter for all sensors. The concentration of each of the measured parameters may be determined and displayed as a percentage of the fluid mixture.

The display 18 may include a movable drain-shaped screen cursor that may be freely oriented on a graphical symbol of the human abdomen to show the physician the actual drain orientation inside the body. The drain-shaped cursor may be manually oriented upon the application of the drain.

In one embodiment, it may be desirable configure the surgical drain 10 to maximize the contact between a sensor 12 and the organ 100. This may be advantageous at least in improving the accuracy of measurements obtained from the organ 100.

Figure 13A:
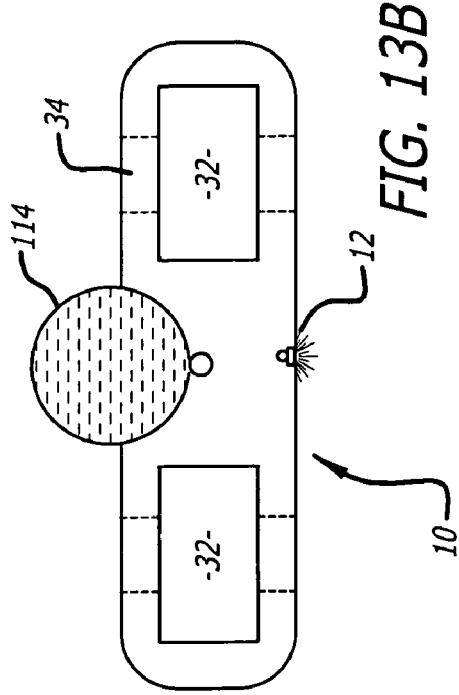
FIGS. 13A & B and 13E & F are schematic diagrams of cross-sectional views of embodiments of surgical drains having an inflatable chamber.
Figure 13B:
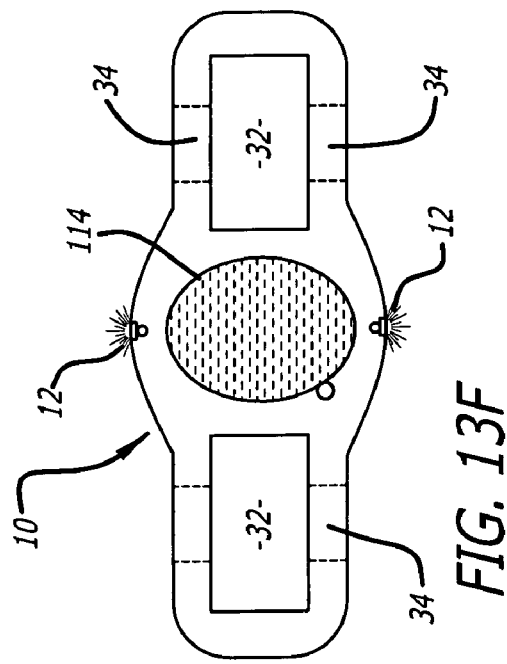
FIGS. 13C & D are schematic depictions of side views of one embodiment a surgical drain having an inflatable chamber and inflation devices.
FIG. 13G is a graphic representation of reflectance intensities received from the sensing system.
Figure 13E:
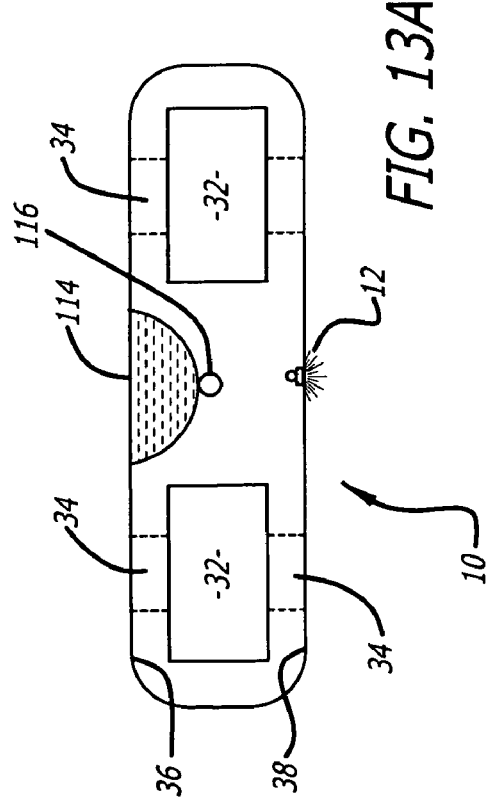
Figure 13F:
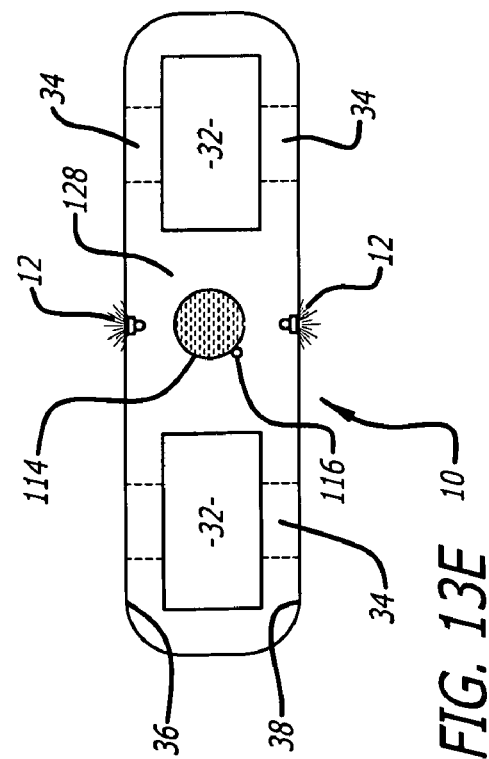
Figure 13G:
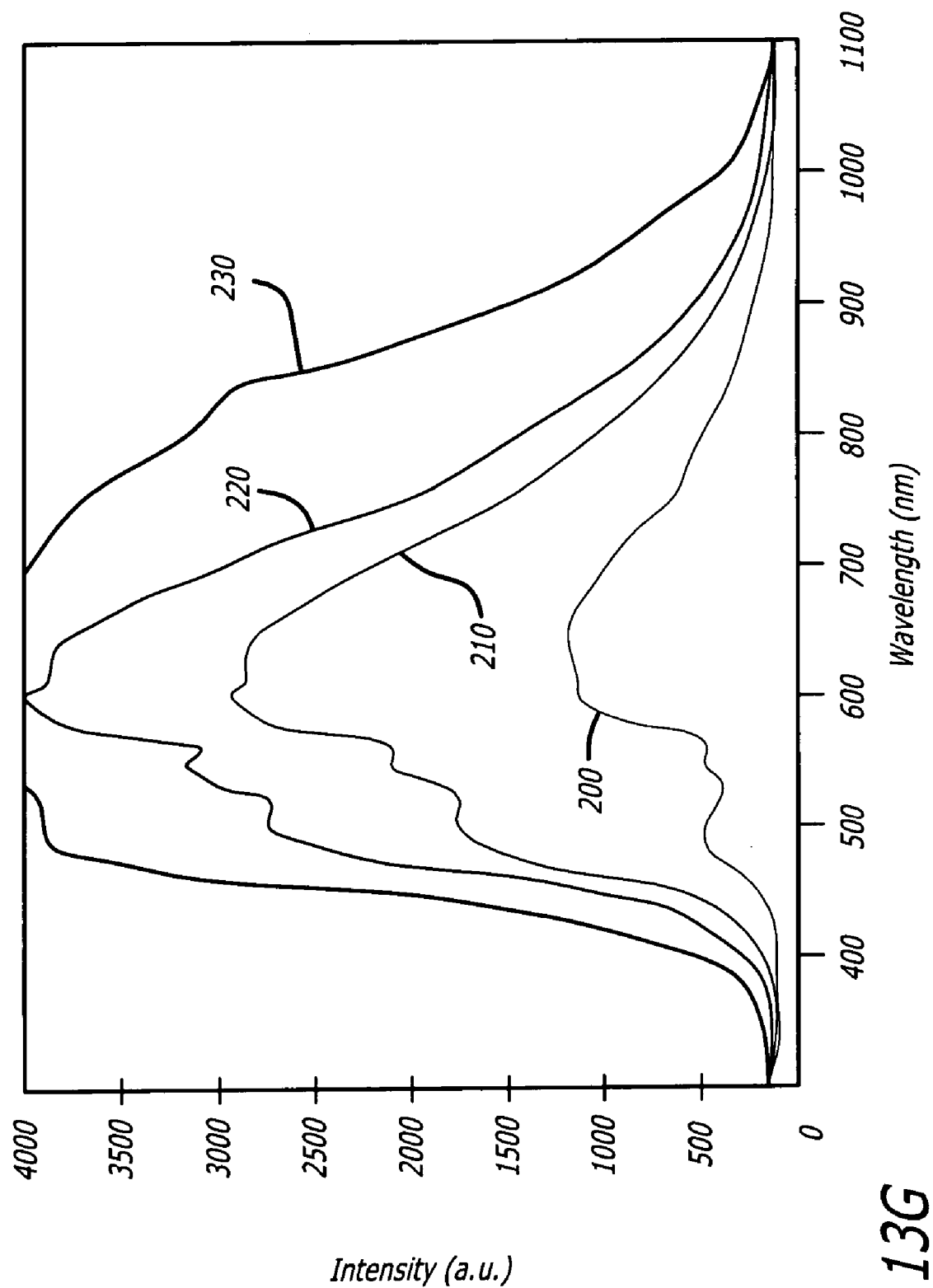

FIGS. 13A & B are schematic diagrams depicting cross-sectional views of one embodiment of a surgical drain 10. FIGS. 13B & C are schematic depictions of side views of a surgical drain 10. In one embodiment, the surgical drain 10 may include at least one inflatable chamber 114, such as balloons within the body of the surgical drain 10. The surgical drain 10 may further include a channel 116 in communication with the interior of the inflatable chamber 114. In one embodiment, a pump 118 may be in communication with the channel 116 and the interior of the inflatable chamber 114. The pump 118 may include a pressure sensor 120 in communication with the inflatable chamber 114 may be used to control the inflation process so that the sensor 12 comes in optimal contact with the organ 100. In one embodiment, the inflatable chamber 114 may be positioned on the surgical drain upper surface 36 approximately opposite a sensor 12 proximate to drain lower surface 38. The inflatable chamber 114 may be expanded by inflation, such as with saline, air or the like such that the inflatable chamber 114 would bulge out and create a force (F) against the adjacent tissue, as shown in FIG. 13C. This force may generate a reaction force (R) that may press the sensor 12 on the drain lower surface 38 against the organ 100.

The inflatable chamber 114 may be left continuously inflated throughout the monitoring period, or temporarily inflated when the sensors 12 are acquiring measurements. The processor 80 may analyze the average intensity and/or spectral features of the reflected light measured at the sensor to determine if the sensor 12 is in optimal contact with the organ 100.

FIGS. 13 E & F are schematic diagrams of a cross-sectional view of an alternative embodiment of a surgical drain including an inflatable compartment 114. The inflatable compartment 114 may be positioned within a central portion of the drain 10, such as within an internal rib 128. Upon inflation, forces may press the drain upper surface 36 and lower surface 38 against tissue 100, thereby improving sensor 12 contact.

FIGS. 14A & B are schematic depictions of a bottom view and a side view of one embodiment of a surgical drain 10. In one embodiment, sensors 12 may be positioned within or upon protrusions 122 which extend from the drain outer surface 26. The protrusions 122 may be integral to the drain body 10 or attached thereto. The protrusions 122 may be made of a transparent material. This configuration may be advantageous in increasing the pressure with which the sensors contact an organ 100.

In use, a surgical drain 10 may be placed within a body cavity proximate to a site of trauma or surgery. The surgical drain 10 may permit the fluid caused by tissue edema, for example, to be drained from the site. To position a surgical drain 10, a physician may, for example, create an incision through which the surgical drain may be implanted. Alternatively, if the patient has been opened for surgery, the drain may be positioned proximate to the surgical site and the body closed around it. The surgical drain 10 may be positioned upon an organ or between tissues of interest, and may be positioned such that sensors 12 contact different regions of a tissue until monitoring is no longer needed, at which time the drain may be pulled out of the body. In one embodiment of the invention, one or more surgical drains 10 may be placed on/in/proximate to an organ 100 to monitor its condition and removed when monitoring is no longer desired, such as at the end of the postoperative monitoring period.

In some embodiments, it may be desirable to stabilize theposition of the drain 10 relative to the tissue, such that the sensors 12 have improved contact with the tissue 100 and/or to increase the likelihood that measurements taken over time will be of the same or similar portion of the tissue 100. Therefore, in some embodiments, the surgical drain 10 may be modified to stabilize its position relative to a monitored organ 100.

The surgical drain 10 may be actively attracted to the surrounding organs/tissue by the continuous negative pressure (suction) in its lumen 32. The negative pressure may also draw wound fluids from the surgical drain 10. External suction may be actively applied to a tube 40 in communication with a surgical drain 10.

FIGS. 15A & B are schematics depicting a plan view and a side view of a surgical drain 10. In one embodiment, the surgical drain 10 may include at least one anchor 124 configured for insertion into a tissue 100 to stabilize the position of the surgical drain 10 within the body. The anchor 124 may be integral to the surgical drain 10 or may be fabricated separately from the surgical drain 10 and connected thereto. The anchor 124 may be in the form of a biologically compatible needle, which may include a beveled distal end for insertion into a tissue 100. The direction of the insertion into a tissue 100 may be opposite to the pullout direction of the surgical drain 10 for smoother removal from the patient.

FIG. 15C is a schematic depicting a plan view of a surgical drain 10. The anchor 124 may be in the form of a loop 124 extending from the surgical drain outer surface 26. In use, a surgeon may utilize the loop as a suture point to attach the surgical drain 10 to a tissue, such as with a resorbable suture.

FIG. 15D is a schematic depicting a bottom view of a surgical drain 10. The anchor 124 may be in the form of biocompatible adhesive 124, such as medical grade pressure sensitive adhesive, or fibrin glue for adhering the surgical drain 10 to the surface of the organ 100.

FIGS. 15E & F are schematics depicting a bottom view and a side view of a surgical drain 10, respectively. The anchor 128 may be in the form of a flap 136 which extends from the drain outer surface 26. The flap 136 may be integral to the drain wall 30 or formed seperately and attached thereto. The flap may be formed of the same material as the drain wall 30. The material may be selected so as to permit flexibility of the flap 136 as it is positioned relative to the tissue 100 or as it is removed from the body 102. The flap may further include a leading edge 130, which may be reinforced to provide a greater thickness at the leading edge 130 than at the remainder of the flap 136. The shape of the flap may be selected so as to enhance the stabilization of the drain 10 relative to the organ 100, and may prevent rotation of the drain 10. The flaps may assume any other shape including square, circular and rectangular. The flaps 136 may also include a layer of adhesive for adhering the flap to a tissue. The flaps 136 may also include sensors 12, if desired.

In one embodiment, there may be flap wings 136 on both sides to stabilize the surgical drain 10 on the surface of the tissue 100. The flap wings may increase the surface area of the drain 10 at the sensor location 12 and hence improve its passive adhesion to the moist surface of an organ. The flaps 136 may be preferably rectangular in shape with their apex pointing in the pullout direction of the drain 10 for smoother removal from the patient. The flaps 136 may have edges 130 that are reinforced against tearing by a thicker silicone layer or by an embedded thread or wire that is continuous into the drain wall 30.

Anchors 124 may be advantageous at least in preventing the surgical drain 10 from moving relative to the organ 100 during use. Further, the anchor 124 may also hold the sensor 12 on the surgical drain outer surface 26 against the surface of the tissue of interest 100. The form of the anchor 124 may be selected to minimize damage to the tissue or organ to which the surgical drain 10 is attached. Further, the anchor may be selected to maximize the stability of the connection between the surgical drain and the target organ, yet minimize the effort and damage caused during surgical drain removal.

In one embodiment, a surgical drain 10 may be placed in the proximity of an organ which has been transplanted, such as a liver, kidney, such that the drain length 20 is positioned longitudinally over the organ 100. This embodiment may be advantageous at least in allowing a physician to monitor the condition of the transplanted organ from the time of surgery through recovery to determine the condition of the organ 100. A physician may use information about the condition of the organ to decide if any further intervention, such as drug treatment (such as antibiotics or immunosuppressants) or retransplantation may be required. This method of monitoring may be advantageous at least in that it may minimize procedures to inspect the organ, enabling detection of organ dysfunction at an early stage, which may allow therapeutic intervention prior to reversible damage, increase implant survival, decrease mortality rate (from infection, organ rejection), decrease the number of organs used for retransplantation, and the additional risk and cost of retransplantation.

While the specification describes particular embodiments of the present invention, those of ordinary skill can devise variations of the present invention without departing from the inventive concept. For example, it will be understood that the invention may also comprise any combination of the embodiments described.

Although now having described certain embodiments of methods and devices of a surgical drain, it is to be understood that the concepts implicit in these embodiments may be used in other embodiments as well. In short, the protection of this application is limited solely to the claims that now follow.

We claim:

1. A surgical drain for sensing a physiological property of at least one tissue and draining fluid from a body comprising:
    a) an elongated conduit configured to be implanted in a patient's body and rest against a first tissue and a second tissue within the body to drain fluid from the patient's body, wherein the elongated conduit comprises a drain portion having openings spaced along substantially the length of the drain portion, wherein the surgical drain is not configured to penetrate either the first or second tissues;
    b) a first sensing element configured to sense a physiological property of the first tissue adjacent to a first location of the elongated conduit; and
    c) a second sensing element configured to sense the same physiological property of the second tissue adjacent to a second location of the elongated conduit different than the first location.

2. The surgical drain of claim 1, wherein the physiological property is selected from the group comprising: temperature, oxygenation, perfusion, pH, NADH levels, biochemical composition, drug concentrations, turgidity or pressure.

3. The surgical drain of claim 1, further including at least one transmitting element configured to deliver energy to the first tissue and the second tissue located proximate to the first and second locations.

4. The surgical drain of claim 1, comprising a third sensing element configured to sense a second physiological property of tissue proximate to the conduit that is different from the physiological property sensed by the first and second sensing elements.

5. The surgical drain of claim 1, wherein at least portions of the first and second sensing elements are embedded within the conduit behind material that is optically transparent.

6. The surgical drain of claim 1, further including a processing system in communication with the first and second sensing elements configured to compare a difference between the physiological property sensed by the first and second sensing elements.

7. The surgical drain of claim 6, wherein the sensing elements sense oxygenation and wherein the processing system is configured to compare the difference between the oxygenation sensed by the first and second sensing elements.

8. The surgical drain of claim 6, wherein said processing system further including a display configured to depict data corresponding to the physiological property sensed by the first or second sensing elements.

9. The surgical drain of claim 1, wherein the conduit further comprises a third sensing element configured to sense the same physiological property of tissue adjacent to a third location of the elongated conduit different from the first and second locations; and a fourth sensing element configured to sense the same physiological property of tissue adjacent to a fourth location of the elongated conduit different from the first, second and third locations.

10. The surgical drain of claim 9, further including a processing system configured to compare a difference between the physiological property sensed by the first, the second, the third and the fourth sensing elements.

11. The surgical drain of claim 1, wherein the first and second sensing elements include optical fibers.

12. The surgical drain of claim 1, wherein the first sensing element includes a component that is affixed to the conduit.

13. The surgical drain of claim 12, wherein the component is embedded in the conduit.

14. The surgical drain of claim 12, wherein the component includes a sensor.

15. The surgical drain of claim 12, wherein the component includes an optical fiber.

16. The surgical drain of claim 1, wherein the first tissue and the second tissue are part of the same organ.

17. The surgical drain of claim 1, wherein the first tissue and the second tissue are not part of the same organ.

18. The surgical drain of claim 1, wherein the first sensing element and the second sensing element are located on the same surface of the elongated conduit.

19. The surgical drain of claim 1, wherein the first sensing element and the second sensing element are located on substantially opposing surfaces of the elongated conduit.

20. A surgical drain for sensing a physiological property of at least one tissue and draining fluid from a body comprising:
    a) an elongated conduit configured to be implanted in a patient's body in proximity to an organ at a first location and to a tissue that is not part of the organ at a second location that is different from the first location, the elongated conduit having a drain portion with openings spaced along substantially its length and configured to drain fluid from the patient's body in the vicinity of the organ and the tissue, wherein the surgical drain is not configured to penetrate either the first or second tissues;

b) a first sensing element coupled to the elongated conduit and configured to sense a physiological property of the organ; and c) a second sensing element coupled to the elongated conduit and configured to separately sense the same physiological property of the tissue.

21. The surgical drain of claim 20, further comprising a processing system configured to compare the physiological property sensed by the first sensing element with the physiological property sensed by the second sensing element.

* * * * *